United States Patent
Choisy et al.

(10) Patent No.: US 10,173,080 B2
(45) Date of Patent: Jan. 8, 2019

(54) DEHYDROASCORBIC ACID OR MONOMERIC, POLYMERIC OR ISOMERIC DERIVATIVE THEREOF AND AN AMINE FOR ARTIFICIALLY COLORING THE SKIN

(75) Inventors: Patrick Choisy, Montlouis sur Loire (FR); Francis Pruche, Senlis (FR)

(73) Assignee: L'Oreal, Paris (FR)

( * ) Notice: Subject to any disclaimer, the term of this patent is extended or adjusted under 35 U.S.C. 154(b) by 976 days.

(21) Appl. No.: 12/685,073

(22) Filed: Jan. 11, 2010

(65) Prior Publication Data

US 2010/0221203 A1    Sep. 2, 2010

Related U.S. Application Data

(63) Continuation of application No. PCT/FR2008/051267, filed on Jul. 7, 2008.

(60) Provisional application No. 60/929,965, filed on Jul. 19, 2007.

(30) Foreign Application Priority Data

Jul. 9, 2007   (FR) ..................... 07 56353

(51) Int. Cl.
| | | |
|---|---|---|
| A61K 8/49 | (2006.01) | |
| A61Q 19/04 | (2006.01) | |
| A61K 8/04 | (2006.01) | |
| A61K 8/06 | (2006.01) | |
| A61K 8/67 | (2006.01) | |

(52) U.S. Cl.
CPC .............. *A61Q 19/04* (2013.01); *A61K 8/042* (2013.01); *A61K 8/062* (2013.01); *A61K 8/064* (2013.01); *A61K 8/676* (2013.01); *A61K 2800/88* (2013.01)

(58) Field of Classification Search
CPC ........ A61K 8/042; A61K 8/062; A61K 8/064; A61K 8/676; A61K 2800/00; A61Q 19/04
See application file for complete search history.

(56) References Cited

U.S. PATENT DOCUMENTS

| | | | | |
|---|---|---|---|---|
| 4,293,543 | A | * | 10/1981 | Cotte et al. ............... 424/59 |
| 5,980,920 | A | * | 11/1999 | Lindquist et al. ........ 424/401 |
| 6,889,870 | B2 | | 5/2005 | De Laforcade |
| 2003/0150069 | A1 | * | 8/2003 | Kleen et al. ............... 8/561 |

FOREIGN PATENT DOCUMENTS

| | | |
|---|---|---|
| DE | 10149007 A1 | 4/2003 |
| EP | 0752843 B1 | 12/2000 |
| EP | 1270444 B2 | 1/2003 |
| FR | 2466492 | 4/1981 |
| FR | 2801788 A2 | 6/2001 |
| WO | WO99/18917 * | 4/1999 ........... A61K 7/00 |
| WO | WO 99/18917 A2 | 4/1999 |
| WO | WO 2005/039510 A2 | 5/2005 |

OTHER PUBLICATIONS

U.S. Appl. No. 09/529,561 (English language translation of Moller WO99/18917).*

* cited by examiner

*Primary Examiner* — Sean M Basquill
(74) *Attorney, Agent, or Firm* — Buchanan Ingersoll & Rooney PC

(57) ABSTRACT

A regime or regimen for artificially coloring the skin entails topically applying thereon at least a) dehydroascorbic acid and/or a monomeric derivative thereof of formula (I) below and/or an isomeric form thereof of formula (I') below and/or a polymeric derivative thereof:

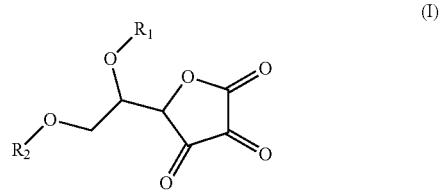

(I)

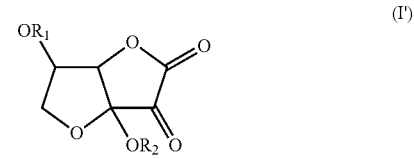

(I')

in which:
  $OR_1$ and $OR_2$, which may be identical or different, are each OH; a saturated or unsaturated, linear or branched $C_1$-$C_{30}$ and more preferentially $C_1$-$C_{18}$ alkoxy radical; a glycoside and more preferentially glucose; an ester of a saturated or unsaturated, linear or branched $C_1$-$C_{30}$ (preferably $C_1$-$C_{18}$) aliphatic carboxylic acid, which may be substituted with an aryl radical or a heterocycle; an aryl or heterocyclic carboxylic acid ester, which may be substituted with at least one saturated or unsaturated, linear or branched $C_1$-$C_{30}$ (more preferentially $C_1$-$C_{18}$) alkyl radical; a phosphate group; a sulfate group, and
b) at least one amine compound.

8 Claims, No Drawings

1

DEHYDROASCORBIC ACID OR MONOMERIC, POLYMERIC OR ISOMERIC DERIVATIVE THEREOF AND AN AMINE FOR ARTIFICIALLY COLORING THE SKIN

CROSS-REFERENCE TO PRIORITY/PROVISIONAL APPLICATIONS

This application claims priority under 35 U.S.C. § 120 of U.S. Provisional Application No. 60/929,965, filed Jul. 19, 2007, and of § 119 of FR 0756353, filed Jul. 9, 2007, and is a continuation/national phase of PCT/FR 2008/0.51267, filed Jul. 7, 2008 and designating the United States (published in the French language on Jan. 22, 2009 as WO 2009/010685 A2; the title and abstract were also published in English), each hereby expressly incorporated by reference in its entirety and each assigned to the assignee hereof.

BACKGROUND OF THE INVENTION

Technical Field of the Invention

The present invention relates to a process for artificially coloring the skin which entails topically applying thereon a composition comprising, in a physiologically acceptable medium, at least dehydroascorbic acid and/or a monomeric derivative thereof of formula (I) that will be defined later and/or an isomer thereof of formula (I') and/or a polymeric and especially dimeric derivative thereof of formula (II) defined later, and at least one compound comprising at least one free amine function.

Description of Background and/or Related and/or Prior Art

Today, it is important to look healthy, and a tanned skin is always a sign of good health. However, a natural tan is not always desirable since it requires long exposure to UV radiation, in particular to UV-A radiation that causes tanning of the skin but, however, is liable to induce an adverse change therein, in particular in the case of sensitive skin or of skin that is continually exposed to solar radiation. It is thus desirable to find an alternative to a natural tan that is compatible with the requirements of such skin types.

Most of the cosmetic products intended for artificially tanning the skin are based on carbonyl derivatives which, by interacting with the free amine functions of the skin, in particular the amino acids, peptides or proteins of the skin, permit the formation of colored products.

To this end, it is known that dihydroxyacetone, or DHA, is a particularly advantageous product which is commonly included in cosmetics as an agent for artificially tanning the skin; when applied to the skin, in particular to the face, it provides a tanning or bronzing effect which is similar in appearance to that which may result from prolonged exposure to sunlight (a natural tan) or under a UV lamp. Moreover, DHA-based products, by providing a tanned, healthy appearance, allow skin imperfections to be concealed.

One drawback of DHA is the length of time the coloration takes to develop: specifically, several hours (3 to 5 hours in general) are required for the coloration to be revealed. Another drawback of DHA is its tendency to produce yellow shades that harm the production of a natural skin tone. There is thus increasing demand for coloring products for the skin that act quickly and provide a coloration closer to that of the natural color of the skin. Moreover, self-tanning agents such as DHA cannot produce an adequate tone on dark skin.

Thus, need continues for novel compounds and novel compositions that can give the skin an artificial coloration close to that of natural skin color in a simple, effective and fast manner, and for any type of dark or fair skin.

WO 2005/039510 discloses the use of dehydroascorbic acid or a salt thereof produced in situ via enzymatic oxidation, as a fixing agent in the permanent waving of hair. DE-19745354 also discloses the use of dehydroascorbic acid in combination with particular compounds with primary or secondary amine groups or hydroxyl groups, for coloring the hair.

SUMMARY OF THE INVENTION

After extensive studies conducted in the field of artificial coloring of the skin, it has now been discovered that dehydroascorbic acid or a polymer thereof in combination with an amino compound can impart, after topical application of the product to the skin, an artificial coloration closer to that of natural pigmentation, which develops more quickly than standard self-tanning agents such as DHA (visible after 30 minutes) and gives stronger colors whose red component is more pronounced, and affording, depending on the quantity used, a range of shades closer to natural pigmentation and for any type of fair or dark skin.

For the purposes of the present invention, the expression "artificial coloration of the skin" means a long-lasting, non-covering coloration (i.e., a coloration that does not have a tendency to opacify the skin), which is not removed either with water or using a solvent, and which is resistant both to rubbing and to washing with a solution containing surfactants. Such a long-lasting coloration is thus distinguished from the superficial and temporary coloration provided, for example, by a makeup product.

For the purposes of the present invention, the term "polymer" means any molecule having in its structure at least two repeating structural units.

For the purposes of the present invention, the expression "physiologically acceptable medium" means any support that is compatible with the skin, the nails, the lips, the eyelashes and the eyebrows, which has a pleasant color, odor and feel and which does not give rise to any unacceptable discomfort (stinging, tautness or redness) liable to put the consumer off using this composition comprising such a support.

Other characteristics, aspects and advantages of the present invention will become apparent from the detailed description that follows.

DETAILED DESCRIPTION OF BEST MODE AND SPECIFIC/PREFERRED EMBODIMENTS OF THE INVENTION

The present invention features a process, whether regime or regimen, for artificially coloring the skin, which entails topically applying a composition comprising, in a physiologically acceptable medium, at least dehydroascorbic acid and/or a monomeric derivative thereof of formula (I) that will be defined later and/or an isomer thereof of formula (I') and/or a polymeric derivative thereof, especially dimers of formula (II) that will be defined later, and at least one compound comprising at least one free amine function.

Dehydroascorbic acid and the monomeric derivatives in accordance with the invention correspond to formula (I) below:

The dehydroascorbic acid derivatives may in particular be selected from among those corresponding to formula (I) below:

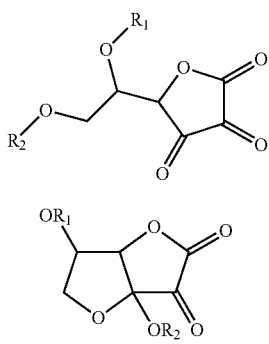

(I)

(I')

in which:

OR$_1$ and OR$_2$, which may be identical or different, are each OH; a linear or branched, saturated or unsaturated C$_1$-C$_{30}$ and more preferentially C$_1$-C$_{18}$ alkoxy radical; a glycoside and more preferentially glucose; a linear or branched, saturated or unsaturated C$_1$-C$_{30}$ (preferably C$_1$-C$_{18}$) aliphatic carboxylic acid ester, which may be substituted with an aryl radical or a heterocycle; an aryl or heterocyclic carboxylic acid ester which may be substituted with at least one linear or branched, saturated or unsaturated C$_1$-C$_{30}$ (more preferentially C$_1$-C$_{18}$) alkyl radical; a phosphate group; a sulfate group.

Preferentially, R$_2$ is a linear or branched, saturated or unsaturated C$_1$-C$_{30}$ (preferably C$_1$-C$_{18}$) aliphatic carboxylic acid ester, which may be substituted with an aryl radical or a heterocycle; an aryl or heterocyclic carboxylic acid ester which may be substituted with at least one linear or branched, saturated or unsaturated C$_1$-C$_{30}$ (more preferentially C$_1$-C$_{18}$) alkyl radical.

Dehydroascorbic acid is also known as threo-2,3-hexodiulosono-1,4-lactone, 9Cl (CAS 490-83-5) and has the structure:

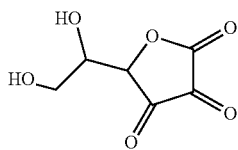

Among the monomeric derivatives of dehydroascorbic acid of formula (I) and (I') that are particularly exemplary are the following compounds:

L-threo-2,3-hexodiulosonic acid, γ-lactone, 5,6-bis(3-phenyl-2-propenoate)
(CAS #106406-96-6) with OR$_1$=OR$_2$=3-phenyl-2-propenoate
L-threo-2,3-hexodiulosonic acid, γ-lactone, 6-acetate
(CAS #106227-02-5) with OR$_2$=acetate and R$_1$=H
L-threo-2,3-hexodiulosonic acid, γ-lactone, 5,6-diacetate
(CAS #59681-41-3) with OR$_1$=OR$_2$=acetate
L-threo-2,3-hexodiulosonic acid, γ-lactone, 6-hexadecanoate
(CAS #63247-05-2) with OR$_2$=hexadecanoate and OR$_1$=H
L-threo-2,3-hexodiulosonic acid, γ-lactone, 6-octadecanoate (9Cl)
(CAS #59681-40-2) with OR$_2$=octadecanoate and OR$_1$=OH
L-threo-2,3-hexodiulosonic acid, γ-lactone, 6-benzoate
(CAS #63247-04-1) with OR$_2$=benzoate and OR$_1$=OH.

Among the examples of polymeric derivatives that are representative are the dimeric compounds of formula (II) below:

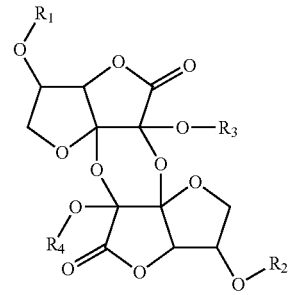

(II)

in which:

OR$_1$, OR$_2$, OR$_3$ and OR$_4$, which may be identical or different, are each OH; a linear or branched, saturated or unsaturated C$_1$-C$_{30}$ and more preferentially C$_1$-C$_{18}$ alkoxy radical; a glycoside and more preferentially glucose; a linear or branched, saturated or unsaturated C$_1$-C$_{30}$ (preferably C$_1$-C$_{18}$) aliphatic carboxylic acid ester, which may be substituted with an aryl radical or a heterocycle; an aryl or heterocyclic carboxylic acid ester which may be substituted with at least one linear or branched, saturated or unsaturated C$_1$-C$_{30}$ (more preferentially C$_1$-C$_{18}$) alkyl radical; a phosphate group; a sulfate group.

Preferentially, R$_1$ and/or R$_2$ will be a linear or branched, saturated or unsaturated C$_1$-C$_{30}$ (preferably C$_1$-C$_{18}$) aliphatic carboxylic acid ester, which may be substituted with an aryl radical or a heterocycle; an aryl or heterocyclic carboxylic acid ester which may be substituted with at least one linear or branched, saturated or unsaturated C$_1$-C$_{30}$ (more preferentially C$_1$-C$_{18}$) alkyl radical.

Among the dehydroascorbic acid-based dimers of formula (II), particularly exemplary are the following compounds:

2H,8H-bisfuro[3',2':2,3]furo[3,4-b:3',4'-e][1,4]dioxin-5,11 (5aH,11aH)-dione,
3,5a,9,11a-tetrakis(benzoyloxy)tetrahydro-[3S-(3α,3aα, 5aβ,6aS*,9aα,11aβ,12aS*)] (CAS #103559-39-3) with OR$_1$=OR$_2$=OR$_3$=OR$_4$=benzoate
1,6,9,13-tetraoxadispiro[4.2.4.2]tetradecane-7,14-dicarboxylic acid, 4,12-dihydroxy-3,7,11,14-tetramethoxy-, di-γ-lactone
(CAS #94329-25-6) with R$_1$=R$_2$=R$_3$=R$_4$=methyl
2H,8H-bisfuro[3',2':2,3]furo[3,4-b:3',4'-e][1,4]dioxin-5,11 (5aH,11aH)-dione,
3,5a,9,11a-tetrakis(acetyloxy)tetrahydro-[3S-(3α,3aα,5aβ, 6aS*,9α,9aα,11aβ,12aS*)] (CAS #25726-18-5) with OR$_1$=OR$_2$=OR$_3$=OR$_4$=acetate
2H,8H-bisfuro[3',2':2,3]furo[3,4-b:3',4'-e][1,4]dioxin-5,11 (5aH,11aH)-dione,
3,5a,9,11a-tetrakis(3"-phenyl-2"-propenoxy)tetrahydro-[3S-(3α,3aα,5aβ,6aS*,9α,9aα,11aβ,12aS*)] (CAS #106406-97-7) with OR$_1$=OR$_2$=OR$_3$=OR$_4$=3-phenyl-2-propenoate.

More particularly exemplary is the dimeric compound (CAS #72691-25-29) with R$_1$=R$_2$=H, having the following structure:

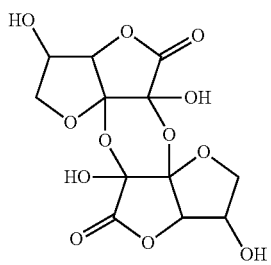

The compounds with a free amine function in accordance with the invention are preferably selected from among amino acids, proteins, oligopeptides, polypeptides and protein hydrolyzates, or mixtures thereof.

Among the amino acids according to the invention, examples thereof include α-amino acids obtained by hydrolysis of animal or plant proteins, for instance collagen, keratin, casein, elastin, soya protein, and wheat or almond glutens. Also exemplary are arginine, glycine, tyrosine, alanine, phenylalanine, dihydroxyphenylalanine (DOPA), ornithine, lysine, polylysines, especially with a molecular weight ranging from 100,000 to 80,000 daltons, spermitine, citrulline, tryptophan, 6-aminocapronic acid, isoleucine, leucine, methionine, serine, proline, valine, hydroxyproline, aspartic acid, tyrosine, taurine, Val-Tyr-Val, L-asparagine, Lys-Lys-Lys-Lys and Cys-Gly.

Among the peptides, exemplary are glutathione (GSH), and collagen, keratin, casein, elastin, soya protein, wheat gluten or almond protein hydrolysates.

Valine, glutamine, glutathione, L-phenylalanine, serine, glycine, Val-Tyr-Val, alanine or methionine are more particularly preferred.

Preferentially, the dehydroascorbic acid or a derivative thereof and the amine compound are stored separately and mixed together at the time of use.

The present invention also features a multi-compartment device, also known as a "kit" or "skin-coloring equipment", comprising at least:

a first compartment comprising a component (A) containing, in a physiologically acceptable medium, at least dehydroascorbic acid and/or a monomeric derivative thereof of formula (I) and/or an isomer thereof of formula (I') and/or a polymeric derivative thereof as defined above, a second compartment comprising component (B) containing at least one amino compound as defined above.

According to a first embodiment of the device in accordance with the invention, components (A) and (B) may be conditioned independently each in a container delimiting at least one compartment, the said container being closed by means of a closing member.

The container may be in any adequate form. It may especially be in the form of a bottle, a tube, a jar, a case, a box, a sachet or a carton.

The closing member may be in the form of a removable stopper, a lid, a cap, a tear-off strip or a capsule, especially of the type comprising a body attached to the container and a cover cap articulated on the body. It may also be in the form of a member for selectively closing the container, especially a pump, a valve or a flap valve.

The product may be contained directly in the container, or indirectly. By way of example, the product may be arranged on an impregnated support, especially in the form of a wipe or a pad, and arranged (individually or in plurality) in a box or in a sachet. Such a support incorporating the product is described, for example, in WO 01/03538.

The closing member may be coupled to the container by screwing. Alternatively, the coupling from the closing member and the container is done other than by screwing, especially via a bayonet mechanism, by click-fastening, gripping, welding, bonding or by magnetic attraction. The term "click-fastening" in particular means any system involving the crossing of a bead or cord of material by elastic deformation of a portion, especially of the closing member, followed by return to the elastically unconstrained position of the said portion after the crossing of the bead or cord.

The container may be at least partially made of thermoplastic material. Examples of such thermoplastic materials include polypropylene or polyethylene.

Alternatively, the container is made of non-thermoplastic material, especially glass or metal (or alloy).

The container may have rigid walls or deformable walls, especially in the form of a tube or a tubular bottle.

The container may comprise means for distributing or facilitating the distribution of the composition. By way of example, the container may have deformable walls so as to cause the composition to exit in response to a positive pressure inside the container, this positive pressure being caused by elastic (or non-elastic) squeezing of the walls of the container.

According to another embodiment, the respective components (A) and (B) are conditioned in two containers that are joined together so as to be securely fastened to each other.

For example, they are contained in two containers held together via an outer packaging. In particular, each container is equipped with a dispensing member, for example a pump or a valve. Preferably, this dispensing member is manually actuated. The pump may also be without an air inlet, in the case where the composition is to be protected from any contact with the exterior, during its storage time.

According to a first embodiment, the actuation of these dispensing members leads the compositions into an assembly mixing chamber, so as to ensure mixing prior to them being dispensed from this assembly formed by these two joined containers.

Alternatively, according to a first embodiment, actuation of these distribution members leads the compositions into a chamber in which the whole is mixed, so as to ensure that they are mixed before being dispensed from this assembly formed by these two joined containers.

Alternatively, according to a second embodiment, the actuation of these dispensing members leads to expulsion of the compositions without premixing.

One particular embodiment of the invention is a device as described in EP-1,270,444. It is a device for the simultaneous dispensing of the two components (A) and (B), conditioned separately in first and second flexible-wall sachets, the said device comprising:

i) means for solidly holding the two sachets in a superposed position such that respective outlet orifices of the said sachets are aligned in the region of each other; and ii) means, which are movable relative to the fixing means, and capable of pressurizing the two sachets so as to force the expulsion of their contents through their respective outlet orifices in a predetermined ratio.

Another particular embodiment of the invention is a device as described in EP-1,300,344. It is a device for the combined dispensing of the two components (A) and (B) conditioned separately, comprising:

a) a first flexible-wall container containing component (A);

b) a second flexible-wall container, outside the first, containing component (B);

c) a stage on which the first and second containers are mounted;

d) a dispensing member, which is movable relative to the stage, and capable of making the device pass, irreversibly, from a first configuration in which the first and second containers are isolated from at least one dispensing orifice formed by the said dispensing member, to a second configuration in which the first and second containers are in communication with the said dispensing orifice(s).

Thus, in the second configuration of the device, in response to a pressure exerted on the flexible walls of the first and second containers, which are arranged adjacent to each other, the first and second products may be dispensed together.

The combined expulsion of the two products in order to prepare a composition, especially a cosmetic composition, may take place via a single dispensing orifice, upstream of which may be located a mixing zone in which the two products are placed in contact before being dispensed in mixed form.

Another particular embodiment of a device of the invention is a twin pump comprising:

a) two reservoirs, which are preferably housed in the same outer housing comprising, respectively, component (A) or component (B), preferably housed in the same outer housing;

b) two pumps, each mounted on a reservoir, c) a single push-button, which is axially movable along a main elongation axis of the outer housing, and which allows the simultaneous opening of the two pumps to be actuated; these two pumps each moreover being connected via an outlet channel emerging at least one dispensing orifice.

The said dispensing orifice may be unique and common to the two reservoirs. In this case, the products exit in mixed form.

According to another embodiment, each outlet channel is associated with its own dispensing orifice. The products contained in these reservoirs are thus dispensed from the device without ever having come into contact beforehand inside the device. This type of variant is especially described in FR-2,789,371; U.S. Pat. No. 5,224,627; WO 97/05040.

Another particular embodiment of a device of the invention is a double aerosol comprising:

a) two reservoirs, preferably housed in the same outer housing comprising at least one propellant and, respectively, component (A) or component (B), b) two aerosol valves, each mounted on a reservoir, c) a single push-button, which is axially movable along a main elongation axis of the outer housing, and allowing the simultaneous opening of the two pumps to be actuated; these two valves each moreover being connected via an outlet channel emerging at least one dispensing orifice.

The said dispensing orifice may be unique and common to the two reservoirs. In this case, the products exit in mixed form.

According to another embodiment, each outlet channel is associated with its own dispensing orifice. The products contained in these reservoirs are then dispensed from the device, without ever having come into contact beforehand inside the device.

Needless to say, depending on the device used, one skilled in the art will take care, for each of components (A) and (B), to select the viscosity and rheological properties that are suitable for allowing good expulsion of the products from the said device.

According to one particular form of the invention, the dehydroascorbic acid may be formed "in situ" from ascorbic acid or a derivative thereof or a salt thereof via chemical oxidation and/or via enzymatic oxidation according to the following reaction scheme:

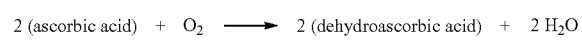

The oxidation reaction may in particular be efficiently catalyzed by many types of enzymes, for instance the ascorbate oxidizes produced by the majority of plants and also certain bacteria, yeasts or animals (E. C [1.10.3.3] Lee, M. N.; Dawson, C. R. Methods Enzymol., 1979, 62, 30-39).

This invention also features a process for artificially coloring the skin, which comprises topically applying thereto a) a first component (C) containing, in a physiologically acceptable medium, at least ascorbic acid or a derivative or salt thereof and at least one compound comprising at least one amine function and b) placing in contact said component (C) with atmospheric oxygen or with a second component (D) containing, in a physiologically acceptable medium, at least one chemical oxidizing agent other than atmospheric oxygen and/or one enzymatic oxidizing agent; components (C) and (D) being mixed together at the time of use, applied simultaneously, or else one after the other to the skin.

According to one embodiment of this process, the amine compound may also be in component (D).

The chemical oxidizing agent used in accordance with the dyeing process of the invention is preferably atmospheric oxygen or a system capable of generating oxygen, for instance hydrogen peroxide or sodium peroxide.

The chemical oxidizing agents other than atmospheric oxygen conventionally used for the oxidation of ascorbic acid or derivatives or salts thereof are, for example, hydrogen peroxide, urea peroxide, alkali metal bromates, persalts such as perborates and persulfates, and peracids, or mixtures thereof.

The enzymatic oxidizing systems used are conventionally oxidize enzymes using either atmospheric oxygen or a substrate to form hydrogen peroxide, among which mention may be made of 2-electron oxidoreductases such as uricases, ascorbate oxidases, etc.

The enzymes used in accordance with the present invention are preferably selected from among the ascorbate oxidases using atmospheric oxygen. More preferentially, the enzymes are selected from among those belonging to the Enzyme Commission classification [1.10.3.3].

The ascorbate oxidase enzyme may be derived, for example, from the following botanic genera: *Arabidopsis, Brassica, Cucumis, Curcubita, Myrothecium, Nicotiana, Oryza, Triticum*. It is more preferentially selected from among those derived from *Curbita pepo mudullosa* (aubergine). It is also possible to use an ascorbate oxidase enzyme obtained from numerous other plants, including cabbage (*Brassica oleracea*), cucumber (*Cucumis savitus*), pumpkin (*Curcubita* cv. *Ebisu Nankin*), tobacco (*Nicotiana tabacum*), mustard (*Sinapsis alba*), rice (*Oryza sativa*) and wheat (*Triticum aestivum*). Other sources include mushrooms (*Myrotectium verrucaria*) and thermophilic bacteria (*Acremonium* sp. HI-25).

The enzyme may be present as a solution or in powder form and may preferably be stabilized with buffers, glycerol, sugars or other polyhydroxylated compounds, metal-chelating agents such as EDTA, thiols such as thioglycerol, mercaptoethanol or dithiothreitol, polyethylene glycol, unreactive proteins or other enzyme-preserving agents. The enzymes may also be stabilized via covalent modification according to standard techniques. The enzyme may also be immobilized by covalent bonding onto a solid support such as surface-modified silica, alumina, glass, oxirane-modified polymethacrylate, carboxyalkylcellulose, aminoalkyl silica, aminoalkyl glass or aminoalkylcellulose microparticles. The enzymes may also be adsorbed onto the surfaces of hydrophobically or ionically modified particles such as carboxyalkylcelluloses or dialkylaminocelluloses. Another possibility consists in covalently bonding the enzyme with a synthetic or biosynthetic water-soluble polymer, such as polyethylene glycols, poly(acrylic acids), poly(vinyl alcohols), polyethyleneimines, dextran and proteins such as gelatin or uricase.

The said enzyme is preferably present in the composition resulting from the mixing of components (C) and (D) in contents ranging from 1 to 10,000 ppm and preferably 100 to 1,000 ppm.

The present invention also features a multi-compartment device, also known as a "kit" or "skin-coloring equipment" comprising at least:

a first compartment comprising component (C) as defined above, and a second compartment comprising component (D) as defined above, the amine compound possibly being either in component (C) or in component (D).

Among the devices that are suitable for this type of coloring process, use may be made of those as described previously.

According to one particular form of the invention, in order to increase the remanence of the color and/or the uniformity of the color obtained after applying dehydroascorbic acid or a monomeric, polymeric or isomeric derivative thereof to the skin, it is combined with ascorbic acid or a derivative or salt thereof.

Another aspect of the invention is a process for artificially coloring the skin, which comprises topically applying to the skin:

a) a component (A) containing, in a physiologically acceptable medium, at least dehydroascorbic acid or a monomeric, polymeric or isomeric derivative thereof as defined previously;

b) a component (B) containing, in a physiologically acceptable medium, at least one amine compound as described previously;

d) a component (C) containing, in a physiologically acceptable medium, ascorbic acid or a derivative or salt thereof;

e) and in placing component (C) in contact with atmospheric oxygen or with a component (D) containing, in a physiologically acceptable medium, at least one chemical oxidizing agent and/or one enzymatic oxidizing agent as defined previously; components (A), (B), (C) and optionally (D) possibly being mixed together at the time of use or being applied to the skin one after the other.

The present invention also features a multi-compartment device, also known as a "kit" or "skin-coloring equipment" selected from among (i) a device comprising at least:
a first compartment comprising component (A) as defined above,
a second compartment comprising component (B) and compound (C) as defined above, and optionally
a third compartment comprising component (D) as defined above.

(ii) a device comprising at least:
a first compartment comprising component (A) and component (C) as defined previously;
a second compartment comprising component (B) and compound (D) as defined previously.

(ii) a device comprising at least:
a first compartment comprising component (A) as defined previously;
a second compartment comprising component (B) as defined previously;
a third compartment comprising component (C) as defined previously, and optionally
a fourth compartment comprising component (D) as defined previously.

Dehydroascorbic acid or a polymeric derivative thereof is preferably used in contents ranging from 0.1% to 50% by weight and more preferentially from 1% to 10% by weight relative to the total weight of the composition containing it.

Ascorbic acid or a derivative or salt thereof is preferably used in contents ranging from 0.1% to 50% by weight and more preferentially from 1% to 15% by weight relative to the total weight of the composition containing it.

The relative proportions of amino acid and of dehydroascorbic acid or derivatives thereof in the compositions of the invention may vary within a wide range as a function of the desired coloration.

The compositions of the invention may be in any form that is suitable for topical application, especially in the form of aqueous gels, in the form of emulsions obtained by dispersing a fatty phase (also known as an oily phase) in an aqueous phase (O/W) or, conversely, (W/O) or multiple emulsions (for example W/O/W, O/W/O or O/O/W). They may be more or less fluid and may have the appearance of a white or colored cream, a pomade, a milk, a lotion, a serum, a paste, a powder or a solid tube, and they may optionally be packaged as an aerosol and be in the form of a mousse or spray. These compositions are prepared according to the usual methods.

According to one particular embodiment of the invention, the compositions of the invention may be in the form of an emulsion and in this case may comprise at least one oily phase. The proportion of the oily phase of the emulsion may range from 1% to 80% by weight, preferably from 2% to 50% by weight and better still from 2% to 40% by weight relative to the total weight of the composition. The fatty substances of the oily phase, especially the oils, and the emulsifiers and coemulsifiers that may be present, used in the composition in emulsion form are selected from among those conventionally used in cosmetics or dermatology. The emulsifier and the coemulsifier, when they are present, are generally in a proportion ranging from 0.1% to 30% by weight, preferably from 0.3% to 20% by weight and better still from 0.5% to 15% by weight relative to the total weight of the composition. The emulsion may also contain lipid vesicles in addition to or instead of the emulsifiers and/or coemulsifiers.

The emulsions generally contain at least one emulsifier selected from among amphoteric, anionic, cationic and nonionic emulsifiers, used alone or as a mixture. The emulsifiers are selected in an appropriate manner according to the continuous phase of the emulsion to be obtained (W/O or O/W). When the emulsion is multiple, it generally comprises an emulsifier in the primary emulsion and an emulsifier in the outer phase into which the primary emulsion is introduced.

As emulsifiers that may be used for the preparation of the W/O emulsions, examples that may be mentioned include alkyl esters or ethers of sorbitan, of glycerol or of sugars; silicone surfactants, for instance dimethicone copolyols such as the mixture of cyclomethicone and of dimethicone copolyol, marketed under the trademarks DC 5225 C and DC 3225 C by Dow Corning, and alkyldimethicone copolyols such as laurylmethicone copolyol marketed under the trademark "Dow Corning 5200 Formulation Aid" by Dow Corning, cetyl dimethicone copolyol marketed under the trademark Abil EM 90® by Goldschmidt, and the mixture of polyglyceryl-4 isostearate/cetyl dimethicone copolyol/hexyl laurate marketed under the trademark Abil WE 09® by Goldschmidt. One or more coemulsifiers may also be added thereto, which may be selected, advantageously, from the group comprising branched-chain fatty acid esters of polyol, and especially branched-chain fatty acid esters of glycerol and/or of sorbitan, for example polyglyceryl isostearate, such as the product marketed under the trademark Isolan GI 34 by Goldschmidt, sorbitan isostearate, such as the product marketed under the trademark Arlacel 987 by ICI, sorbitan glyceryl isostearate, such as the product marketed under the trademark Arlacel 986 by ICI, and mixtures thereof.

As emulsifiers that may be used for the preparation of the O/W emulsions, examples that may be mentioned include nonionic emulsifiers such as fatty acid esters of oxyalkylenated (more particularly polyoxyethylenated) polyols, for example polyethylene glycol stearates, for instance PEG-100 stearate, PEG-50 stearate and PEG-40 stearate; fatty acid esters of oxyalkylenated sorbitan comprising, for example, from 20 to 100 EO, for example those marketed under the trademarks Tween 20 or Tween 60 by Uniqema; oxyalkylenated (oxyethylenated and/or oxypropylenated) fatty alkyl ethers; alkoxylated or non-alkoxylated sugar esters, for instance sucrose stearate such as PEG-20 methylglucose sesquistearate; sorbitan esters such as the sorbitan palmitate marketed under the trademark Span 40 by Uniqema; diacid esters of fatty alcohols, for instance dimyristyl tartrate; mixtures of these emulsifiers, for instance the mixture of glyceryl stearate and of PEG-100 stearate (CTFA name: Glyceryl Stearate/PEG-100 Stearate) marketed under the trademark Arlacel 165 by Uniqema and under the trademark Simulsol 165 by SEPPIC; or the mixture of dimyristyl tartrate, cetearyl alcohol, Pareth-7 and PEG-25 laureth-25, marketed under the trademark Cosmacol PSE by Sasol (CTFA name: Dimyristyl tartrate/cetearyl alcohol/12-15 Pareth 7/PPG 25 laureth 25).

Coemulsifiers such as, for example, fatty alcohols having from 8 to 26 carbon atoms, for instance cetyl alcohol, stearyl alcohol and the mixture thereof (cetearyl alcohol), octyldodecanol, 2-butyloctanol, 2-hexyldecanol, 2-undecylpentadecanol or oleyl alcohol, or fatty acids, may be added to these emulsifiers.

It is also possible to prepare emulsions without emulsifying surfactants or containing less than 0.5% of them relative to the total weight of composition (A) or (B), by using suitable compounds, for stabilizing the said emulsions, for example amphiphilic polymers or electrolytes.

When the composition of the invention is in emulsion form, it comprises at least one oily phase that contains at least one oil, especially a cosmetic oil. The term "oil" means a fatty substance that is liquid at room temperature (25° C.).

As oils that may be used in the composition of the invention, it is possible to use, for example, hydrocarbon-based oils of animal origin, such as perhydrosqualene (or squalane); hydrocarbon-based oils of plant origin, such as caprylic/capric acid triglycerides, for instance those marketed by Stearineries Dubois or those marketed under the trademarks Miglyol 810, 812 and 818 by Dynamit Nobel, or alternatively oils of plant origin, for instance sunflower oil, corn oil, soybean oil, marrow oil, grapeseed oil, sesame seed oil, hazelnut oil, apricot oil, *macadamia* oil, arara oil, coriander oil, castor oil, avocado oil, jojoba oil and shea butter oil; synthetic oils; silicone oils, for instance volatile or non-volatile polymethylsiloxanes (PDMSs) containing a linear or cyclic silicone chain, which are liquid or pasty at room temperature; fluoro oils, such as partially hydrocarbon-based and/or silicone-based fluoro oils, for instance those described in document. JP-A-2 295 912; ethers, such as dicaprylyl ether (CTFA name: Dicaprylyl ether); $C_{12}$-$C_{15}$ fatty alkyl benzoates (Finsolv TN from Finetex); arylalkyl benzoate derivatives, for instance 2-phenylethyl benzoate (X-Tend 226 from ISP); and amido oils, for instance isopropyl N-lauroylsarcosinate (Eldew SL-205 from Ajinomoto); and mixtures thereof.

The composition of the invention may also contain one or more organic solvents that may be selected from among the group consisting of hydrophilic organic solvents, lipophilic organic solvents and amphiphilic solvents, or mixtures thereof.

Examples of hydrophilic organic solvents that may be mentioned include linear or branched monohydric alcohols having from 1 to 8 carbon atoms, for instance ethanol, propanol, butanol, isopropanol or isobutanol; polyethylene glycols having from 6 to 80 ethylene oxides; polyols such as propylene glycol, isoprene glycol, butylene glycol, glycerol or sorbitol; monoalkyl or dialkyl isosorbides in which the alkyl groups contain from 1 to 5 carbon atoms, for instance dimethyl isosorbide; glycol ethers, for instance diethylene glycol monomethyl ether or monoethyl ether and propylene glycol ethers, for instance dipropylene glycol methyl ether.

Amphiphilic organic solvents that may be mentioned include polypropylene glycol (PPG) derivatives such as fatty acid esters of polypropylene glycol, and derivatives of PPG and of fatty alcohols, for instance PPG-23 oleyl ether, and PPG-36 oleate.

Examples of lipophilic organic solvents that may be mentioned include fatty esters such as diisopropyl adipate, dioctyl adipate or alkyl benzoates.

The compositions in accordance with the present invention may also comprise standard cosmetic adjuvants selected from among softeners, humectants, opacifiers, stabilizers, emollients, silicones, antifoams, fragrances, preserving agents, anionic, cationic, nonionic, zwitterionic or amphoteric surfactants, fillers, polymers, propellants, and acidifying or basifying agents, or any other ingredient usually used in cosmetics and/or dermatology.

Hydrophilic thickeners that may be mentioned include carboxyvinyl polymers such as carbopols (carbomers) and the Pemulen products (acrylate/C10-C30-alkylacrylate copolymer) and homopolymers and copolymers of acrylamide and/or of 2-acrylamido-2-methylpropanesulfonic acid (AMPS), for instance sodium polyacryloyldimethyltaurate (and) polysorbate 80 (and) sorbitan oleate marketed under the trademark Simulgel 800 by SEPPIC; cellulose derivatives such as hydroxyethylcellulose; polysaccharides and especially gums such as xanthan gum; and mixtures thereof.

Lipophilic thickeners that may be mentioned include modified clays such as hectorite and derivatives thereof, for instance the products marketed under the trademark Bentone.

Preserving agents that may be mentioned include parahydroxybenzoic acid esters, also known as Parabens® (in particular methyl paraben, ethyl paraben and propyl paraben), phenoxyethanol, formaldehyde generators, for instance imidazolidinylurea or diazolidinylurea, chlorhexidine digluconate, sodium benzoate, caprylyl glycol, iodopropynyl butyl carbamate, pentylene glycol, alkyltrimethylammonium bromides such as myristyltrimethylammonium bromide (CTFA name: myrtrimonium bromide), dodecyltrimethylammonium bromide, hexadecyltrimethylammonium bromide, and mixtures thereof such as the mixture marketed under the trademark Cetrimide® by FEF Chemicals. The preserving agent may be present in the composition according to the invention in a content ranging from 0.001% to 10% by weight, especially ranging from 0.1% to 5% by weight and in particular ranging from 0.2% to 3% by weight relative to the total weight of the composition.

According to one particular form of the invention, in order to improve the stability of the dehydroascorbic acid or a polymer thereof and/or that of ascorbic acid or a salt or derivative thereof, each of these active agents may be encapsulated according to standard encapsulation techniques.

The processes for artificially coloring the skin may be applied to the various fair or dark skin types.

These skin types may be classified on the basis of their reactivity to the effects of solar radiation according to the scale proposed by Fitzpatrick.

According to this scale, the various existing skin types may be distinguished according to the following types:

| Type | Skin reactivity | Origin |
| --- | --- | --- |
| I | Always burns, never tans | Celtic |
| II | Always burns, tans very little | Germanic |
| III | Burns moderately, tans gradually | European |
| IV | Burns lightly, tans very easily | Mediterranean |
| V | Rarely burns, tans deeply | Middle Eastern - South American |
| VI | Never burns, highly pigmented | African |

According to one particular embodiment of the invention, the process is intended for caring for people with dark skin (especially of prototypes IV to VI).

According to another embodiment of the invention, the process is intended for caring for people with fair skin (especially of phototypes I to III).

In order to improve the stability of dehydroascorbic acid or a polymer thereof and/or that of ascorbic acid or a salt or derivative thereof, the composition comprising dehydroascorbic acid or a monomeric, polymeric or isomeric derivative thereof and/or the composition comprising ascorbic acid or a salt or derivative thereof and/or the composition comprising the amine compound in accordance with the invention containing them may also include one or more stabilizers.

Examples of stabilizers that may be mentioned include:
chelating agents,
non-crosslinked N-vinylimidazole polymers or copolymers such as those described in EP-1,316,302.

According to the invention, the expression "non-crosslinked N-vinylimidazole polymer or copolymer" means any polymer comprising N-vinylimidazole units, and not comprising a crosslinking agent. Copolymers that are suitable for use in the invention are, for example, copolymers comprising N-vinylimidazole units and N-vinylpyrrolidone and/or N-vinylcaprolactam units.

In one advantageous aspect of the invention, the copolymer has a mole fraction of N-vinylimidazole units of from 0.1 and 1 and more preferentially from 0.4 and 0.9.

According to one advantageous aspect of the invention, the mole ratio from the N-vinylimidazole unit equivalent and the oxidation-sensitive hydrophilic active agent ranges from 0.004 and 16 and preferentially from 0.01 and 1.

An N-vinylimidazole/N-vinylpyrrolidone copolymer will preferentially be used.

The weight-average molar mass of the N-vinylimidazole polymers will advantageously be from 1,000 and $1 \times 10^7$ and preferably from 5,000 and $5 \times 10^6$.

The vinylpyrrolidone/vinylimidazole (50/50) copolymer with a weight-average molar mass of 1,200,000 marketed under the reference Luvitec VPI 55K72W by BASF or the vinylpyrrolidone/vinylimidazole (50/50) copolymer with a weight-average molar mass of 10,000 marketed under the reference Luvitec VPI 55K18P by BASF may be used for this purpose. The polymers or copolymers according to the invention may be prepared, for example, according to the method described in WO 97/45517.

(4) amphiphilic polymers selected from among polyisobutylene-based oligomers or polymers comprising a polyisobutylene apolar portion containing at least 40 carbon atoms and at least one polar end portion constituted of carboxylic or dicarboxylic acids, anhydrides thereof or modified forms thereof in the form of esters, amides or salts, and mixtures thereof as described in EP-1,481,677.

These amphiphilic polymers are constituted of a polyisobutylene apolar portion and of at least one polar portion.

The polyisobutylene apolar portion contains at least 40 carbon atoms and preferably from 60 to 700 carbon atoms. It is important for this portion to contain at least 40 carbon atoms in order to achieve the aim of the invention. If there are fewer than 40 carbon atoms, a satisfactorily stable system is not obtained.

The polar portion of these amphiphilic polymers or oligomers is constituted of carboxylic or dicarboxylic acids, anhydrides thereof or modified forms thereof in the form of esters, amides or salts, and mixtures thereof. Preferably, the polar end portion is constituted of dicarboxylic acids or anhydrides thereof or of modified forms thereof in the form of esters, amides or salts.

The expression "modified forms in the form of esters, amides or salts" is carboxylic or dicarboxylic acids modified with alcohols, amines, alkanolamines or polyols, or alternatively in the form of alkali metal, alkaline-earth metal or ammonium salts or alternatively in the form of salts of an organic base, for instance the diethanolamine and triethanolamine salts.

The oligomers or polymers derived from succinic acid or anhydride may be selected especially from the polyisobutylene derivatives of succinic acid or anhydride described in U.S. Pat. Nos. 4,234,435, 4,708,753, 5,129,972, 4,931,110, 4,919,179 and GB-A-2,156,799. The polyisobutylene portion may be hydrogenated or non-hydrogenated, with a molecular weight ranging from 400 to 5,000. In the succinic-terminated polyisobutylene thus obtained, the succinic portion may be esterified, amidated or in salt form, i.e., it may be advantageously modified with alcohols, amines, alkanolamines or polyols, or alternatively may be in the form of alkali metal, alkaline-earth metal or ammonium salts or alternatively in the form of a salt of an organic base, for instance the diethanolamine and triethanolamine salts. The esterified or amidated succinic-terminated polyisobutylenes are products of reaction of (a) a polyisobutylene containing succinic end groups, and (b) an amine or an alcohol, to form an amide or an ester. The term "amine" used herein includes all types of amines, including alkanolamines. They may be, for example, primary, secondary or tertiary monoamines, these amines possibly being aliphatic, cycloaliphatic, aromatic or heterocyclic, and saturated or unsaturated. Moreover, the alcohols may be monoalcohols or polyalcohols. The monoalcohols comprise primary, secondary or tertiary aliphatic alcohols, and phenols. The polyalcohols may be selected, for example, from aliphatic, cycloaliphatic, aromatic and heterocyclic polyalcohols. The modified (esterified or amidated) succinic-terminated polyisobutylenes and the process for preparing them are described in particular in U.S. Pat. No. 4,708,753.

Succinic-terminated polyisobutylenes that may especially be mentioned include modified succinic-terminated polyisobutylenes, such as the products marketed under the trademarks Lubrizol 5603 and Lubrizol 2650 by Lubrizol. According to one preferred embodiment of the invention, the polymer marketed under the trademark Lubrizol 5603 by Lubrizol, which is the diethylethanolamine salt of esterified succinic-terminated polyisobutylene (INCI name: Hydroxyethyldiethonium polyisobutenyl triethylaminosuccinate/diethylethanolamine), is used.

Another example of a polyisobutylene derivative that may be used in the invention is the product of reaction of maleic anhydride with polyisobutylene, such as the product marketed under the trademark Glissopal SA by BASF.

(5) maleic anhydride copolymers comprising one or more maleic anhydride comonomers and one or more comonomers selected from among vinyl acetate, vinyl alcohol, vinylpyrrolidone, olefins having from 2 to 20 carbon atoms and styrene, as described in EP-1,374,849.

According to the invention, the term "maleic anhydride copolymer" means any polymer obtained by copolymerization of one or more maleic anhydride comonomers and of one or more comonomers selected from among vinyl acetate, vinyl alcohol, vinylpyrrolidone, olefins having from 2 to 20 carbon atoms, for instance octadecene, ethylene, isobutylene, diisobutylene, isooctylene, and styrene, the maleic anhydride comonomers being optionally partially or totally hydrolysed. Preferably, hydrophilic polymers will be used, i.e., polymers with a solubility in water of greater than or equal to 2 g/l.

Copolymers that are more particularly suitable for use in the invention are copolymers obtained by copolymerization of one or more maleic anhydride units, whose maleic anhydride units are in hydrolysed form, and preferentially in the form of alkaline salts, for example in the form of ammonium, sodium, potassium or lithium salts.

In one advantageous aspect of the invention, the copolymer has a mole fraction of maleic anhydride units of from 0.1 to 1 and more preferentially from 0.4 to 0.9.

According to one advantageous aspect of the invention, the mole ratio from the maleic anhydride unit equivalent and the oxidation-sensitive hydrophilic active agent ranges from 0.005 and 10 and preferentially from 0.01 and 1.

The weight-average molar mass of the maleic anhydride copolymers will advantageously be from 1,000 and 500,000 and preferably from 1,000 and 50,000.

Preferentially, a copolymer of styrene and of maleic anhydride in a 50/50 ratio will be used.

The styrene/maleic anhydride (50/50) copolymer, in the form of the ammonium salt at 30% in water, marketed under the reference SMA1000H® by Atofina, or the styrene/maleic anhydride (50/50) copolymer, in the form of the sodium salt at 40% in water, marketed under the reference SMA1000HNa® by Atofina, may be used, for example.

In order to improve the photostability of dehydroascorbic acid or of a polymer thereof and/or that of ascorbic acid or a salt or derivative thereof, the composition comprising dehydroascorbic acid or a monomeric, polymeric or isomeric derivative thereof and/or the composition comprising ascorbic acid or a salt or derivative thereof and/or the composition comprising the amine compound in accordance with the invention containing them may also include one or more photoprotective agents.

The photoprotective agents in accordance with the invention are selected from among UV-A-active and/or UV-B-active organic and/or mineral UV-screening agents that are hydrophilic and/or lipophilic and/or insoluble in the commonly used cosmetic solvents.

The hydrophilic, lipophilic or insoluble organic UV-screening agents are selected especially from anthranilates; dibenzoylmethane derivatives; cinnamic derivatives; salicylic derivatives; camphor derivatives; benzophenone derivatives; β,β-diphenylacrylate derivatives; triazine derivatives; benzotriazole derivatives; benzalmalonate derivatives, especially those cited in U.S. Pat. No. 5,624,663; benzimidazole derivatives; imidazolines; bis-benzazolyl derivatives as described in EP,669,323 and U.S. Pat. No. 2,463,264; p-aminobenzoic acid (PABA) derivatives; methylenebis(hydroxyphenylbenzotriazole) derivatives as described in U.S. Pat. Nos. 5,237,071, 5,166,355, GB-2,303, 549, DE-197,26,184 and EP-893,119; benzoxazole derivatives as described in EP-0,832,642, EP-1,027,883, EP-1, 300,137 and DE-101,62,844; screening polymers and screening silicones such as those described especially in WO 93/04665; α-alkylstyrene-based dimers, such as those described in DE-198,55,649; 4,4-diarylbutadienes such as those described in EP-0,967,200, DE-197,46,654, DE-197, 55,649, EP-A-1,008,586, EP-1,133,980 and EP-133,981, and mixtures thereof.

As examples of organic UV-screening agents, mention may be made of those denoted hereinbelow under their INCI name:

Para-Aminobenzoic Acid Derivatives:
PABA,
Ethyl PABA,
Ethyl dihydroxypropyl PABA,
Ethylhexyl dimethyl PABA marketed in particular under the trademark
"Escalol 507" by ISP,
Glyceryl PABA,
PEG-25 PABA marketed under the trademark "Uvinul P25" by BASF.

Dibenzoylmethane Derivatives:
Butylmethoxydibenzoylmethane marketed especially under the trademark "Parsol 1789" by Hoffmann LaRoche,
Isopropyldibenzoylmethane.

Salicylic Derivatives:
Homosalate marketed under the trademark "Eusolex HMS" by Rona/EM Industries,
Ethylhexyl salicylate marketed under the trademark "Neo Heliopan OS" by Haarmann and Reimer,
Dipropylene glycol salicylate marketed under the trademark "Dipsal" by Scher,
TEA salicylate marketed under the trademark "Neo Heliopan TS" by Haarmann and Reimer.

Cinnamic Derivatives:
Ethylhexyl methoxycinnamate marketed in particular under the trademark "Parsol MCX" by Hoffmann LaRoche,
Isopropyl methoxycinnamate,
Isoamyl methoxycinnamate marketed under the trademark "Neo Heliopan E 1000" by Haarmann and Reimer,
Cinoxate,
DEA methoxycinnamate,
Diisopropyl methylcinnamate,
Glyceryl ethylhexanoate dimethoxycinnamate.

β,β-Diphenylacrylate Derivatives:
Octocrylene marketed in particular under the trademark "Uvinul N539" by BASF,
Etocrylene marketed in particular under the trademark "Uvinul N35" by BASF.

Benzophenone Derivatives:
Benzophenone-1 marketed under the trademark "Uvinul 400" by BASF,
Benzophenone-2 marketed under the trademark "Uvinul D50" by BASF,
Benzophenone-3 or Oxybenzone marketed under the trademark "Uvinul M40" by BASF,
Benzophenone-4 marketed under the trademark "Uvinul MS40" by BASF,
Benzophenone-5,
Benzophenone-6 marketed under the trademark "Helisorb 11" by Norquay,
Benzophenone-8 marketed under the trademark "SpectraSorb UV-24" by American Cyanamid,
Benzophenone-9 marketed under the trademark "Uvinul DS-49" by BASF,
Benzophenone-12
n-hexyl 2-(4-diethylamino-2-hydroxybenzoyl)benzoate.

Benzylidenecamphor Derivatives:
3-Benzylidenecamphor manufactured under the trademark "Mexoryl SD" by Chimex,
4-Methylbenzylidenecamphor marketed under the trademark "Eusolex 6300" by Merck,
Benzylidenecamphorsulfonic acid manufactured under the trademark "Mexoryl SL" by Chimex,
Camphor benzalkonium methosulfate manufactured under the trademark "Mexoryl SO" by Chimex,
Terephthalylidenedicamphorsulfonic acid manufactured under the trademark "Mexoryl SX" by Chimex,
Polyacrylamidomethylbenzylidenecamphor manufactured under the trademark "Mexoryl SW" by Chimex.

Phenylbenzimidazole Derivatives:
Phenylbenzimidazolesulfonic acid marketed in particular under the trademark "Eusolex 232" by Merck,
Disodium phenyl dibenzimidazole tetrasulfonate marketed under the trademark "Neo Heliopan AP" by Haarmann and Reimer.

Phenylbenzotriazole Derivatives:
Drometrizole trisiloxane marketed under the trademark "Silatrizole" by Rhodia Chimie,
Methylenebis(benzotriazolyl)tetramethylbutylphenol marketed in solid form under the trademark "MIXXIM BB/100" by Fairmount Chemical, or in micronized form as an aqueous dispersion under the trademark "Tinosorb M" by Ciba Specialty Chemicals.

Triazine Derivatives:
bis-Ethylhexyloxyphenol methoxyphenyl triazine marketed under the trademark Tinosorb S by Ciba Geigy, Ethylhexyl triazone marketed in particular under the trademark Uvinul T150 by BASF,
Diethylhexyl butamido triazone marketed under the trademark Uvasorb HEB by Sigma 3V,
2,4,6-tris(Dineopentyl 4'-aminobenzalmalonate)-s-triazine the symmetrical triazine screening agents described in U.S. Pat. No. 6,225,467, WO 2004/085 412 (see compounds 6 and 9) or the document "Symmetrical Triazine Derivatives" IP.COM Journal, IP.COM INC WEST HENRIETTA, N.Y., US (20 Sep. 2004), especially 2,4,6-tris(biphenyl)-1,3,5-triazines (in particular 2,4,6-tris(biphenyl-4-yl-1,3,5-triazine) and 2,4,6-tris(terphenyl)-1,3,5-triazine which is also mentioned in WO 06/035,000, WO 06/034,982, WO 06/034,991, WO 06/035,007, WO 2006/034,992 and WO 2006/034,985.

Anthranilic Derivatives:
Menthyl anthranilate marketed under the trademark "Neo Heliopan MA" by Haarmann and Reimer.

Imidazoline Derivatives:
Ethylhexyldimethoxybenzylidenedioxoimidazoline propionate.

Benzalmalonate Derivatives:
Dineopentyl 4'-methoxybenzalmalonate
Polyorganosiloxane containing benzalmalonate functions, for instance Polysilicone-15, marketed under the trademark "Parsol SLX" by Hoffmann LaRoche 4,4-Diarylbutadiene Derivatives:
1,1-Dicarboxy(2,2'-dimethylpropyl)-4,4-diphenylbutadiene Benzoxazole Derivatives:
2,4-bis[5-(1-dimethylpropyl)benzoxazol-2-yl(4-phenyl)imino]-6-(2-ethylhexyl)imino-1,3,5-triazine marketed under the trademark Uvasorb K2A by Sigma 3V and mixtures thereof.

The preferential organic UV-screening agents are selected from among:
Ethylhexyl methoxycinnamate,
Homosalate,
Ethylhexyl salicylate,
Octocrylene,
Phenylbenzimidazolesulfonic acid,
Benzophenone-3,
Benzophenone-4,
Benzophenone-5,
n-Hexyl 2-(4-diethylamino-2-hydroxybenzoyl)benzoate,
4-Methylbenzylidenecamphor,
Terephthalylidenedicamphorsulfonic acid,
Disodium phenyldibenzimidazoletetrasulfonate,
Ethylhexyl triazone,
bis-Ethylhexyloxyphenol methoxyphenyl triazine,
Diethylhexyl butamido triazone,
2,4,6-tris(Dineopentyl 4'-aminobenzalmalonate)-s-triazine,
2,4,6-tris(Diisobutyl 4'-aminobenzalmalonate)-s-triazine,
2,4,6-tris(Biphenyl-4-yl-1,3,5-triazine), 2,4,6-tris(Terphenyl)-1,3,5-triazine
Methylenebis(benzotriazolyl)tetramethylbutylphenol,
Drometrizole trisiloxane,
Polysilicone-15,
Dineopentyl 4'-methoxybenzalmalonate,
1,1-Dicarboxy(2,2'-dimethylpropyl)-4,4-diphenylbutadiene,
2,4-bis[5-1(Dimethylpropyl)benzoxazol-2-yl(4-phenyl)imino]-6-(2-ethylhexyl)imino-1,3,5-triazine,
and mixtures thereof.

The inorganic screening agents are selected from among pigments (mean size of the primary particles: generally from 5 nm and 100 nm and preferably from 10 nm and 50 nm) of coated or uncoated metal oxides, for instance nanopigments of titanium oxide (amorphous or crystallized in rutile and/or anatase form), of iron oxide, of zinc oxide, of zirconium oxide or of cerium oxide, which are all UV photoprotective agents that are well known per se.

The pigments may be coated or uncoated.

The coated pigments are pigments that have undergone one or more surface treatments of chemical, electronic, mechanochemical and/or mechanical nature with compounds as described, for example, in Cosmetics & Toiletries, February 1990, Vol. 105, pp. 53-64, such as amino acids, beeswax, fatty acids, fatty alcohols, anionic surfactants, lecithins, sodium, potassium, zinc, iron or aluminum salts of fatty acids, metal alkoxides (of titanium or of aluminum), polyethylene, silicones, proteins (collagen, elastin), alkanolamines, silicon oxides, metal oxides or sodium hexametaphosphate.

As is known, silicones are organosilicon polymers or oligomers of linear or cyclic, branched or crosslinked structure, of variable molecular weight, obtained by polymerization and/or polycondensation of suitably functionalized silanes, and consist essentially of a repetition of main units in which the silicon atoms are linked together via oxygen atoms (siloxane bond), optionally substituted hydrocarbon-based radicals being directly attached via a carbon atom to the said silicon atoms.

The term "silicones" also includes the silanes required for their preparation, in particular alkyl silanes.

The silicones used for coating the pigments that are suitable for the present invention are preferably selected from among the group containing alkyl silanes, polydialkylsiloxanes and polyalkylhydrogenosiloxanes. Even more preferentially, the silicones are selected from among the group containing octyltrimethylsilane, polydimethylsiloxanes and polymethylhydrogenosiloxanes.

Needless to say, before being treated with silicones, the metal oxide pigments may have been treated with other surface agents, in particular with cerium oxide, alumina, silica, aluminum compounds or silicon compounds, or mixtures thereof.

The coated pigments are more particularly titanium oxides that have been coated:

with silica, such as the product "Sunveil" from the company Ikeda, with silica and iron oxide, such as the product "Sunveil F" from the company Ikeda, with silica and alumina, such as the products "Microtitanium Dioxide MT 500 SA" and "Microtitanium Dioxide MT 100 SA" from the company Tayca, "Tioveil" from the company Tioxide and "Mirasun TiW 60" from the company Rhodia, with alumina, such as the products "Tipaque TTO-55 (B)" and "Tipaque TTO-55 (A)" from the company Ishihara and "UVT 14/4" from the company Kemira, with alumina and aluminum stearate, such as the product "Microtitanium Dioxide MT 100 T, MT 100 TX, MT 100 Z and MT-01 from the company Tayca, the products "Solaveil CT-10 W" and "Solaveil CT 100" from the company Uniqema, and the product "Eusolex T-AVO" from the company Merck, with silica, alumina and alginic acid, such as the product "MT-100 AQ" from the company Tayca, with alumina and aluminum laurate, such as the product "Microtitanium Dioxide MT 100 S" from the company Tayca, with iron oxide and iron stearate, such as the product "Microtitanium Dioxide MT 100 F" from the company Tayca, with zinc oxide and zinc stearate, such as the product "BR351" from the company Tayca, with silica and alumina and treated with a silicone, such as the products "Microtitanium Dioxide MT 600 SAS", "Microtitanium Dioxide MT 500 SAS" or "Microtitanium Dioxide MT 100 SAS" from the company Tayca, with silica, alumina and aluminum stearate and treated with a silicone, such as the product "STT-30-DS" from the company Titan Kogyo, with silica and treated with a silicone, such as the product "UV-Titan X 195" from the company Kemira, with alumina and treated with a silicone, such as the products "Tipaque TTO-55 (S)" from the company Ishihara or "UV Titan M 262" from the company Kemira, with triethanolamine, such as the product "STT-65-S" from the company Titan Kogyo, with stearic acid, such as the product "Tipaque TTO-55 (C)" from the company Ishihara, with sodium hexametaphosphate, such as the product "Microtitanium Dioxide MT 150 W" from the company Tayca.

Other titanium oxide pigments treated with a silicone are preferably $TiO_2$ treated with octyltrimethylsilane and for which the mean size of the elementary particles is from 25 to 40 nm, such as the product marketed under the trademark "T 805" by Degussa Silices, $TiO_2$ treated with a polydimethylsiloxane and for which the mean size of the elementary particles is 21 nm, such as the product marketed under the trademark "70250 Cardre UF $TiO_2SI_3$" by Cardre, anatase/rutile $TiO_2$ treated with a polydimethylhydrogenosiloxane and for which the mean size of the elementary particles is 25 nm, such as the product marketed under the trademark "Microtitanium Dioxide USP Grade Hydrophobic" by Color Techniques.

The uncoated titanium oxide pigments are marketed, for example, by Tayca under the trademarks "Microtitanium Dioxide MT 500 B" or "Microtitanium Dioxide MT 600 B", by Degussa under the trademark "P 25", by Wackher under the trademark "Transparent titanium oxide PW", by Myoshi Kasei under the trademark "UFTR", by Tomen under the trademark "ITS" and by Tioxide under the trademark "Tioveil AQ".

The uncoated zinc oxide pigments are, for example:

those marketed under the trademark "Z-Cote" by Sunsmart;

those marketed under the trademark "Nanox" by Elementis;

those marketed under the trademark "Nanogard WCD 2025" by Nanophase Technologies.

The coated zinc oxide pigments are, for example:

those marketed under the trademark "Zinc Oxide CS-5" by Toshibi (ZnO coated with polymethylhydrogenosiloxane);

those marketed under the trademark "Nanogard Zinc Oxide FN" by Nanophase Technologies (as a 40% dispersion in Finsolv TN, $C_{12}$-$C_{15}$ alkyl benzoate);

those marketed under the trademark "Daitopersion ZN-30" and "Daitopersion ZN-50" by Daito (dispersions in cyclopolymethylsiloxane/oxyethylenated polydimethylsiloxane, containing 30% or 50% of nanozinc oxides coated with silica and polymethylhydrogenosiloxane);

those marketed under the trademark "NFD Ultrafine ZNO" by Daikin (ZnO coated with perfluoroalkyl phosphate and copolymer based on perfluoroalkylethyl as a dispersion in cyclopentasiloxane);

those marketed under the trademark "SPD-Z1" by Shin-Etsu (ZnO coated with silicone-grafted acrylic polymer, dispersed in cyclodimethylsiloxane);

those marketed under the trademark "Escalol Z100" by ISP (alumina-treated ZnO dispersed in an ethylhexyl methoxycinnamate/PVP-hexadecene/methicone copolymer mixture);

those marketed under the trademark "Fuji ZnO-SMS-10" by Fuji Pigment (ZnO coated with silica and polymethylsilsesquioxane);

those marketed under the trademark "Nanox Gel TN" by Elementis (ZnO dispersed at a concentration of 55% in $C_{12}$-$C_{15}$ alkyl benzoate with hydroxystearic acid polycondensate).

The uncoated cerium oxide pigments are marketed under the trademark "Colloidal Cerium Oxide" by Rhone-Poulenc.

The uncoated iron oxide nanopigments are marketed, for example, by Arnaud under the trademarks "Nanogard WCD 2002 (FE 45B)", "Nanogard Iron FE 45 BL AQ", "Nanogard FE 45R AQ" and "Nanogard WCD 2006 (FE 45R)" or by Mitsubishi under the trademark "TY-220".

The coated iron oxide pigments are marketed, for example, by Arnaud under the trademarks "Nanogard WCD 2008 (FE 45B FN)", "Nanogard WCD 2009 (FE 45B 556)", "Nanogard FE 45 BL 345" and "Nanogard FE 45 BL" or by BASF under the trademark "Transparent Iron Oxide".

Mention may also be made of mixtures of metal oxides, especially of titanium dioxide and of cerium dioxide, including the silica-coated equal-weight mixture of titanium dioxide and of cerium dioxide, marketed by Ikeda under the trademark "Sunveil A", and also the alumina, silica and silicone-coated mixture of titanium dioxide and of zinc dioxide, such as the product "M 261" marketed by Kemira, or the alumina, silica and glycerol-coated mixture of titanium dioxide and of zinc dioxide, such as the product "M 211" marketed by Kemira.

The photoprotective agents are generally present in the compositions containing dehydroascorbic acid or a polymer thereof and/or the compositions comprising ascorbic acid or a salt or derivative thereof in proportions ranging from 0.01% to 20% by weight relative to the total weight of the composition, and preferably ranging from 0.1% to 10% by weight relative to the total weight of the composition.

In order to increase the remanence of the skin color and/or the color homogeneity, the composition comprising dehydroascorbic acid or a monomeric, polymeric or isomeric derivative thereof and/or the composition comprising ascorbic acid or a salt or derivative thereof and/or the composition comprising the amine compound according to the invention may also additionally comprise a wetting agent and/or penetrant, for instance urea, hydroxyethylurea, polyols such as glycerol, alkylene glycols such as propylene glycol or butylene glycol, and alkylene glycol alkyl ethers such as propylene glycol monoethyl ether.

In order to tint the color obtained via the various artificial coloring processes as described above and to better adapt it to the different types of skin tone, the composition comprising dehydroascorbic acid or a monomeric, polymeric or isomeric derivative thereof and/or the composition comprising ascorbic acid or a salt or derivative thereof and/or the composition comprising the amine compound in accordance with the present invention may also comprise one or more additional coloring agents.

The additional coloring agents may be selected especially from natural and synthetic direct dyes. They may be organic or mineral dyes.

The mineral coloring agents may be, for example, iron oxide pigments, the average fundamental particle size of which is less than 100 nm, such as those described in EP-966,953.

The natural or synthetic liposoluble organic dyes are, for example, DC Red 17, DC Red 21, DC Red 27, DC Green 6, DC Yellow 11, DC Violet 2, DC Orange 5, Sudan red, carotenes (β-carotene or lycopene), xanthophylls (capsanthin, capsorubin or lutein), palm oil, Sudan brown, quinoline yellow, annatto and curcumin.

The natural or synthetic water-soluble dyes are, for example, FDC Red 4, DC Red 6, DC Red 22, DC Red 28, DC Red 30, DC Red 33, DC Orange 4, DC Yellow 5, DC Yellow 6, DC Yellow 8, FDC Green 3, DC Green 5, FDC Blue 1, betanin (beetroot), carmine, copper-containing chlorophylline, methylene blue, anthocyanins (enocyanin, black carrot, hibiscus or elder) and riboflavin.

The dyes may also be selected from among anthraquinones, caramel, carmine, carbon black, azulene blues, methoxalene, trioxalene, guajazulene, chamuzulene, rose Bengal, cosine 10B, cyanosin, daphinine, juglone, lawsone, extracts of fermented soya, of algae, of fungi or of microorganisms, flavylium salts not substituted in position 3, for instance those described in EP-1,172,091, extracts of Gesneria fulgens, Blechum procerum or Saxifraga and pigments that may be obtained by extraction with an organic or aqueous-organic solvent of a culture medium of micromycetes of the *Monascus* genus or of actinomycetes of the *Actinomyces* genus.

The compositions according to the invention comprising dehydroascorbic acid or a monomeric, polymeric or isomeric derivative thereof and/or ascorbic acid or a salt or derivative thereof and/or the amino compound may moreover comprise one or more additional cosmetic or dermatological active agents.

The additional active agents may be selected especially from moisturizers, desquamating agents, agents for improving the barrier function, depigmenting agents, antioxidants, dermo-decontracting agents, anti-glycation agents, agents for stimulating the synthesis of dermal and/or epidermal macromolecules and/or for preventing their degradation, agents for stimulating fibroblast or keratinocyte proliferation and/or keratinocyte differentiation, agents for promoting the maturation of the horny envelope, NO-synthase inhibitors, peripheral benzodiazepine receptor (PBR) antagonists, agents for increasing the activity of the sebaceous glands, agents for stimulating the energy metabolism of cells, tensioning agents, lipo-restructuring agents, slimming agents, agents for promoting the cutaneous capillary circulation, calmatives and/or anti-irritants, sebo-regulators or anti-seborrhoeic agents, astringents, cicatrizing agents, anti-inflammatory agents and antiacne agents.

Needless to say, one skilled in the art will take care to select this or these optional additional compound(s), and/or the amount thereof, such that the advantageous properties of the corresponding composition according to the invention are not, or are not substantially, adversely affected by the envisaged addition.

In order to further illustrate the present invention and the advantages thereof, the following specific examples are given, it being understood that same are intended only as illustrative and in nowise limitative. In said examples to follow, all parts and percentages are given by weight, unless otherwise indicated.

Examples of such compounds are described below.

Moisturizers or Humectants:

Moisturizers or humectants that may especially be mentioned include glycerol and derivatives thereof, urea and derivatives thereof, especially Hydrovance® marketed by National Starch, lactic acid, hyaluronic acid, AHAs, BHAs, sodium pidolate, xylitol, serine, sodium lactate, ectoin and derivatives thereof, chitosan and derivatives thereof, collagen, plankton, an extract of *Imperata cylindra* marketed under the trademark Moist 24® by Sederma, acrylic acid homopolymers, for instance Lipidure-HM® from NOF Corporation, beta-glucan and in particular sodium carboxymethyl beta-glucan from Mibelle-AG-Biochemistry; a mixture of passionflower oil, apricot oil, corn oil and rice bran oil marketed by Nestlé under the trademark NutraLipids®; a C-glycoside derivative such as those described in WO 02/051,828 and in particular C-β-D-xylopyranoside-2-hydroxypropane in the form of a solution containing 30% by weight of active material in a water/propylene glycol mixture (60/40% by weight) such as the product marketed by Chimex under the trademark Mexoryl SBB®; an oil of musk rose marketed by Nestlé; an extract of the microalga *Prophyridium cruentum* enriched with zinc, marketed by Vincience under the trademark Algualane Zinc®; spheres of collagen and of chondroitin sulfate of marine origin (Atelocollagen) marketed by Engelhard Lyon under the trademark Marine Filling Spheres; hyaluronic acid spheres such as those marketed by Engelhard Lyon.

The moisturizer that will preferably be used is selected from among urea and derivatives thereof, especially Hydrovance® marketed by National Starch, hyaluronic acid, AHAs, BHAs, acrylic acid homopolymers, for instance Lipidure-HM® from NOF Corporation, beta-glucan and in particular sodium carboxymethyl beta-glucan from Mibelle-AG-Biochemistry; a mixture of passionflower oil, apricot oil, corn oil and rice bran oil marketed by Nestlé under the trademark NutraLipids®; a C-glycoside derivative such as those described in WO 02/051,828 and in particular C-β-D-xylopyranoside-2-hydroxypropane in the form of a solution containing 30% by weight of active material in a water/propylene glycol mixture (60/40% by weight) such as the product marketed by Chimex under the trademark Mexoryl SBB®; an oil of musk rose marketed by Nestlé; an extract of the microalga *Prophyridium cruentum* enriched with zinc, marketed by Vincience under the trademark Algualane Zinc®; spheres of collagen and of chondroitin sulfate of marine origin (Atelocollagen) marketed by Engelhard Lyon under the trademark Marine Filling Spheres; hyaluronic acid spheres such as those marketed by Engelhard Lyon.

Desquamating Agents:

The term "desquamating agent" means any compound capable of acting:

either directly on desquamation by promoting exfoliation, such as β-hydroxy acids (BHAs), in particular salicylic acid and derivatives thereof (including 5-n-octanoylsalicylic acid, also known as capryloyl salicylic acid as the INCI name); α-hydroxy acids (AHAs), such as glycolic acid, citric acid, lactic acid, tartaric acid, malic acid or mandelic acid; 8-hexadecene-1,16-dicarboxylic acid or 9-octadecenedioic acid; urea and derivatives thereof; gentisic acid and derivatives thereof; oligofucoses; cinnamic acid; *Saphora japonica* extract; resveratrol, and certain jasmonic acid derivatives;

or on the enzymes involved in the desquamation or degradation of corneodesmosomes, glycosidases, stratum corneum chymotryptic enzyme (SCCE) or other proteases (trypsin, chymotrypsin-like). Mention may be made of aminosulfonic compounds and in particular 4-(2-hydroxyethyl)piperazine-1-propanesulfonic acid (HEPES); 2-oxothiazolidine-4-carboxylic acid (procysteine) and derivatives thereof; derivatives of α-amino acids of glycine type (as described in EP-0,852,949, and also sodium methyl glycine diacetate marketed by BASF under the trademark Trilon M); honey; sugar derivatives such as O-octanoyl-6-D-maltose and N-acetylglucosamine.

As other desquamating agents that may be used in the composition according to the invention, mention may be made of:

oligofructoses, EDTA and derivatives thereof, *laminaria* extracts, O-linoleyl-6D-glucose, (3-hydroxy-2-pentylcyclopentyl)acetic acid, glycerol trilactate, O-octanyl-6'-D-maltose, S-carboxymethylcysteine, siliceous derivatives of salicylate such as those described in EP-0,796,861, oligofucases such as those described in EP-0,218,200,5-acyl salicylic acid salts, active agents with effects on transglutaminase, as in EP-0,899,330, extract of the flowers of Ficus *Opuntia indica* (Exfolactive® from Silab), 8-hexadecene-1,16-dicarboxylic acid, esters of glucose and of vitamin F, and mixtures thereof.

Preferred desquamating agents that may be mentioned include β-hydroxy acids such as 5-n-octanoyl salicylic acid; urea; glycolic acid, citric acid, lactic acid, tartaric acid, malic acid or mandelic acid; 4-(2-hydroxyethyl)piperazine-1-propanesulfonic acid (HEPES); extract of *Saphora japonica*; honey; N-acetyl glucosamine; sodium methyl glycine diacetate, and mixtures thereof.

Even more preferentially, a desquamating agent selected from among 5-n-octanoyl salicylic acid; urea; 4-(2-hydroxyethyl)piperazine-1-propanesulfonic acid (HEPES); extract of *Saphora japonica*; honey; N-acetyl glucosamine; sodium methyl glycine diacetate, and mixtures thereof, will be used in the compositions of the invention.

Agents for Improving the Barrier Function:

As agents for improving the barrier function, mention may be made especially of arginine, serine, an extract of *Thermus thermophilus* such as Venuceane® from Sederma, an extract of the rhizome of wild yam (*Dioscorea villosa*) such as Actigen Y® from Active Organics, plankton extracts, for instance Omega Plankton® from Secma, yeast extracts, for instance Relipidium® from Coletica, a chestnut extract such as Recoverine® from Silab, a cedar bud extract such as Gatuline Zen from Gattefossé, sphingosines, for instance salicyloyl sphingosine marketed under the trademark Phytosphingosine® SLC by Degussa, a mixture of xylitol, polyxylityl glycoside and xylitan, for instance Aquaxyl® from SEPPIC, extracts of Solanacea plants, for instance Lipidessence® from Coletica, omega-3 unsaturated oils such as musk rose oils, and mixtures thereof.

Mention may also be made especially of ceramides or derivatives thereof, in particular ceramides of type 2 (for instance N-oleoyldihydrosphingosine), of type 3 (for instance stearoyl-4-hydroxysphinganine, as the INCI name) and of type 5 (for instance N-2-hydroxypalmitoyldihydrosphingosine, having the INCI name: hydroxypalmitoyl sphinganine), sphingoid-based compounds, glycosphingolipids, phospholipids, cholesterol and derivatives thereof, phytosterols, essential fatty acids, diacylglycerol, 4-chromanone and chromone derivatives, petroleum jelly, lanolin, shea butter, cocoa butter and PCA salts.

As preferred agents having a restructuring effect on the barrier function, mention will be made of an extract of *Thermus thermophilus*, an extract of wild yam rhizome (*Dioscorea villosa*), a yeast extract, a chestnut extract, a cedar bud extract, arginine, serine, ceramides especially of type 3 and 5; and mixtures thereof.

Serine, arginine or a mixture thereof will preferably be used.

Depigmenting Agents:

Depigmenting agents that may especially be mentioned include alpha and beta arbutin, ferulic acid, lucinol and derivatives thereof, kojic acid, resorcinol and derivatives thereof, tranexamic acid and derivatives thereof, gentisic acid, homogentisate, methyl gentisate or homogentisate, dioic acid, calcium D-pantheteine sulfonate, lipoic acid, ellagic acid, vitamin B3, linoleic acid and derivatives thereof, ceramides and homologues thereof, plant derivatives, for instance camomile, bearberry, the aloe family (vera, ferox, bardensis), mulberry or skullcap; a kiwi fruit (*Actinidia chinensis*) juice marketed by Gattefosse, an extract of *Paeonia suffruticosa* root, such as the product marketed by Ichimaru Pharcos under the trademark Botanpi Liquid B®, an extract of brown sugar (*Saccharum officinarum*), such as the extract of molasses marketed by Taiyo Kagaku under the trademark Molasses Liquid, without this list being exhaustive.

Preferred depigmenting agents that will be used include alpha and beta arbutin, ferulic acid, kojic acid, resorcinol and derivatives thereof, calcium D-pantheteine sulfonate, lipoic acid, ellagic acid, vitamin B3, a kiwi fruit (*Actinidia chinensis*) juice marketed by Gattefosse, and an extract of *Paeonia suffruticosa* root, such as the product marketed by Ichimaru Pharcos under the trademark Botanpi Liquid B®.

Antioxidants:

Mention may be made especially of tocopherol and esters thereof, in particular tocopheryl acetate; ferulic acid; serine; ellagic acid, phloretin, polyphenols, tannins, tannic acid, epigallocatechins and natural extracts containing them, anthocyans, rosemary extracts, olive leaf extracts, for instance those from the company Silab, green tea extracts, resveratrol and derivatives thereof, ergothioneine, N-acetyl-cysteine, an extract of the brown alga *Pelvetia caniculata*, for instance Pelvetiane® from Secma, chlorogenic acid, biotin, chelating agents, such as BHT and BHA, N,N'-bis(3,4,5-trimethoxybenzyl)ethylenediamine and salts thereof; idebenone, plant extracts, for instance Pronalen Bioprotect™ from the company Provital; coenzyme Q10, bioflavonoids, SODs, phytanetriol, lignans, melatonin, pidolates, glutathione, caprylyl glycol, Totarol™ or extract of *Podocarpus totara* containing Totarol (totara-8,11,13-trienol or 2-phenanthrenol, 4b,5,6,7,8,8a,9,10-octahydro-4-b,8,8-trimethyl-1-(1-methylethyl)-; a jasmine extract such as the product marketed by Silab under the trademark Helisun®; hesperitin laurate such as Flavagrum PEG® from the company Engelhard Lyon; an extract of *Paeonia suffruticosa* root, such as the product marketed by Ichimaru Pharcos under the trademark Botanpi Liquid B®; an extract of lychee such as the extract of lychee pericarp marketed by Cognis under the trademark Litchiderm LS 9704®, an extract of pomegranate fruit (*Punica granatum*), such as the product marketed by Draco Natural Products.

Other anti-aging agents that may be mentioned include DHEA and derivatives thereof, boswellic acid, rosemary extracts, carotenoids (β-carotene, zeaxanthin and lutein), cysteic acid, copper derivatives and jasmonic acid.

Preferred antioxidants that will especially be used include ferulic acid; serine; phloretin, an extract of pomegranate (*Punica granatum*), biotin, chelating agents such as BHT, BHA, N,N'-bis(3,4,5-trimethoxybenzyl)ethylenediamine and salts thereof, caprylyl glycol, Totarol™, a jasmine extract such as the product marketed by Silab under the trademark Helisun®; hesperitin laurate such as Flavagrum PEG® from the company Engelhard Lyon; an extract of *Paeonia suffruticosa* root, such as the product marketed by Ichimaru Pharcos under the trademark Botanpi Liquid B®.

Dermo-Relaxing or Dermo-Decontracting Agents:

Examples that may be mentioned include manganese gluconate and other salts, adenosine, alverine citrate and salts thereof, glycine, an extract of *Iris paffida*, a hexapeptide (Argeriline R from Lipotec) or sapogenins, for instance wild yam and the carbonyl amines described in EP-1,484,052. Examples of sapogenins that may be mentioned include those described in WO 02/47650, in particular wild yam, the diosgenin extracted especially from *Dioscorea opposita* or any extract naturally containing or containing after treatment one or more sapogenins (wild yam rhizome, agave leaf, which contains hecogenin and tigogenin, extracts of Liliacea plants and more particularly yucca or smilax containing smilagenin and sarsapogenin, or sarsaparilla) or Actigen Y from the company Actives Organics, or ginger (*Zingiber officinale*).

Mention may also be made of DMAE (dimethyl MEA), extracts of sea fennel, of rockrose, of *helichrysum*, of aniseed, of paracress, and an extract of *Acmella oleracea*, for instance Gatuline® from Gattefossé.

Preferred dermo-relaxing agents that will be mentioned include adenosine, manganese gluconate, wild yam, sea fennel, glycine and alverine.

Anti-Glycation Agents:

The term "anti-glycation agent" means a compound that prevents and/or reduces the glycation of skin proteins, in particular dermal proteins such as collagen.

Anti-glycation agents that may especially be mentioned include extracts of plants of the Ericacea family, such as an extract of blueberry (*Vaccinium angustifolium* or *Vaccinium myrtillus*), for example the product marketed under the trademark Blueberry Herbasol Extract PG by Cosmetochem, ergothioneine and derivatives thereof, hydroxystilbenes and derivatives thereof, such as resveratrol and 3,3',5,5'-tetrahydroxystilbene (these anti-glycation agents are described in FR-2,802,425, FR-2,810,548, FR-2,796,278 and FR-2,802, 420, respectively), dihydroxystilbenes and derivatives thereof, polypeptides of arginine and of lysine such as the product marketed under the trademark Amadorine® by Solabia, carsinine hydrochloride (marketed by Exsymol under the trademark Alistin®), an extract of *Helianthus annuus*, for instance Antiglyskin® from Silab, wine extracts such as the extract of powdered white wine on a maltodextrin support marketed under the trademark Vin blanc déshydraté 2F by Givaudan, thioctic acid (or alpha-lipoic acid), a mixture of extract of bearberry and of marine glycogen, for instance Aglycal LS 8777® from Laboratoires Sérobiologiques, and an extract of black tea, for instance Kombuchka® from Sederma, and mixtures thereof.

Preferred anti-glycation agents that will be mentioned include extracts of blueberry (*Vaccinium myrtillus*) and extracts of black tea (*Camellia sinensis*).

Agents for Stimulating the Synthesis of Dermal and/or Epidermal Macromolecules and/or for Preventing their Degradation:

Among the active agents for stimulating the dermal macromolecules or for preventing their degradation, mention may be made of those acting:

either on collagen synthesis, such as extracts of *Centella asiatica*, asiaticosides and derivatives thereof; ascorbic acid or vitamin C and derivatives thereof; synthetic peptides such as iasmin (*Jasminum grandiflorum*), biopeptide CL or palmitoyl oligopeptide marketed by Sederma; peptides extracted from plants, such as the soybean hydrolysate (*Glycine max*) marketed by Coletica under the trademark Phytokine®; rice peptides such as Nutripeptide® from Silab, methylsilanol mannuronate such as Algisium C® marketed by Exsymol; plant hormones such as auxins and lignans; folic acid; and an extract of Luzerne (*Medicago sativa*) such as the product marketed by Silab under the trademark Vitanol®; a peptide extract of hazelnut such as the product marketed by Solabia under the trademark Nuteline C®; and arginine;

or on the inhibition of collagen degradation, in particular agents acting on the inhibition of metalloproteases (MMP) more particularly such as MMP 1, 2, 3 and 9. Mention may be made of: retinoids and derivatives, extracts of *Medicago sativa* such as Vitanol® from Silab, an extract of *Aphanizomenon flos-aquae* (Cyanophyceae) marketed under the trademark Lanablue® by Atrium Biotechnologies, oligopeptides and lipopeptides, lipoamino acids, the malt extract marketed by Coletica under the trademark Collalift®; blueberry or rosemary extracts; lycopene; isoflavones, derivatives thereof or plant extracts containing them, in particular extracts of soybean (marketed, for example, by Ichimaru Pharcos under the trademark Flavosterone SB®), of red clover, of flax or of kakkon; an extract of lychee such as the extract of lychee pericarp marketed by Cognis under the trademark Litchiderm LS 9704®; Dipalmitoyl Hydroxyproline marketed by SEPPIC under the trademark Sepilift DPHP®: *Baccharis genistelloides* or Baccharine marketed by Silab, an extract of moring a such as Arganyl LS 9781® from Cognis; the sage extract described in FR-A-2,812,544 from the Labiatae family (*Salvia officinalis* from the company Flacksmann), an extract of rhododendron, a blueberry extract, and an extract of *Vaccinium myrtillus* such as those described in FR-A-2,814,950;

or on the synthesis of molecules belonging to the elastin family (elastin and fibrillin), such as: retinol and derivatives, in particular retinyl palmitate; the extract of *Saccharomyces cerevisiae* marketed by LSN under the trademark Cytovitin®; and the extract of the alga *Macrocystis pyrifera* marketed by Secma under the trademark Kelpadelie®; a peptide extract of hazelnut such as the product marketed by Solabia under the trademark Nuteline C®;

or on inhibition of elastin degradation, such as the peptide extract of seeds of *Pisum sativum* marketed by LSN under the trademark Parelastyl®; heparinoids; and the N-acylamino acid compounds described in WO 01/94381, such as {2-[acetyl(3-trifluoromethylphenyl)amino]-3-methylbutyrylamino}acetic acid, also known as N—[N-acetyl, N'-(3-trifluoromethyl)phenylvalyl]glycine, or N-acetyl-N-[3-(trifluoromethyl)phenyl]valylglycine or acetyl trifluoromethylphenylvalylglycine, or an ester thereof with a $C_1$-$C_6$ alcohol; an extract of rice peptides such as Colhibin® from Pentapharm, or an extract of *Phyllanthus emblica* such as Emblica® from Rona;

or on the synthesis of glycosaminoglycans, such as the product of fermentation of milk with *Lactobacillus* vulgaris, marketed by Brooks under the trademark Biomin Yoghurt®; the extract of the brown alga *Padina pavonica* marketed by Alban Müller under the trademark HSP3®; the *Saccharomyces cerevisiae* extract available especially from the company Silab under the trademark Firmalift® or from the company LSN under the trademark Cytovitin®; an extract of *Laminaria ochroleuca* such as Laminaine® from Secma; essence of Mamaku from Lucas Meyer, and an extract of Cress (Odraline® from Silab);

or on the synthesis of fibronectin, such as the extract of the zooplankton Salina marketed by Seporga under the trademark GP4G®; the yeast extract available especially from the company Alban Müller under the trademark Drieline®; and the palmitoyl pentapeptide marketed by Sederma under the trademark Matrixyl®.

Among the active agents for stimulating epidermal macromolecules, such as fillagrin and keratins, mention may be made especially of the extract of lupin marketed by Silab under the trademark Structurine®; the extract of *Fagus sylvatica* beech buds marketed by Gattefosse under the trademark Gatuline® RC; and the extract of the zooplankton Salina marketed by Seporga under the trademark GP4G®; the copper tripeptide from Procyte; a peptide extract of *Voandzeia substerranea* such as the product marketed by Laboratoires Serobiologiques under the trademark Filladyn LS 9397®.

Preferably, an active agent that stimulates the synthesis of dermal and/or epidermal macromolecules and/or that prevents their degradation, selected from among agents for stimulating the synthesis of glycosaminoglycans, agents for inhibiting elastin degradation, agents for stimulating fibronectin synthesis, agents for stimulating the synthesis of epidermal macromolecules, and mixtures thereof, will be used.

Even more preferentially, an active agent that stimulates the synthesis of the glycosaminoglycans, selected from among an extract of the brown alga *Padina pavonica*, an extract of *Saccharomyces cerevisiae*, an extract of *Laminaria ochroleuca*, essence of Mamaku, and an extract of cress, and mixtures thereof, will be used.

As preferred active agents for stimulating the synthesis of dermal and/or epidermal macromolecules and/or for preventing their degradation, mention may be made of:

synthetic peptides such as iamin, the biopeptide CL or palmitoyloligopeptide marketed by Sederma; peptides extracted from plants, such as the soybean hydrolysate marketed by Coletica under the trademark Phytokine®; rice peptides such as Nutripeptide® from Silab, methylsilanol mannuronate such as Algisium C® marketed by Exsymol; folic acid; an extract of lucerne (*Medicago sativa*), such as the product marketed by Silab under the trademark Vitanol®; a peptide extract of hazelnut, such as the product marketed by Solabia under the trademark Nuteline C®; arginine; an extract of *Aphanizomenon flos-aquae* (Cyanophyceae) marketed under the trademark Lanablue® by Atrium Biotechnologies, the malt extract marketed by Coletica under the trademark Collalift®, lycopene; an extract of lychee; an extract of moring a such as Arganyl LS 9781® from Cognis; an extract of *Vaccinium* myrtillus such as those described in FR-A-2,814,950; retinol and derivatives thereof, in particular retinyl palmitate; the extract of *Saccharomyces cerevisiae* marketed by LSN under the trademark Cytovitin®; a peptide extract of hazelnut such as the product marketed by Solabia under the trademark Nuteline C®; {2-[acetyl (3-trifluoromethylphenyl)amino]-3-methylbutyrylamino}acetic acid, also known as N—[N-acetyl, N'-(3-trifluoromethyl)phenylvalyl]glycine, or N-acetyl-N-[3-(trifluoromethyl)phenyl]valylglycine or acetyl trifluoromethylphenylvalylglycine, or an ester thereof with a $C_1$-$C_6$ alcohol; an extract of rice peptides such as Colhibin® from Pentapharm, or an extract of *Phyllanthus emblica* such as Emblica® from Rona; the extract of the brown alga *Padina pavonica* marketed by Alban Müller under the trademark HSP3®; the extract of *Saccharomyces cerevisiae* available especially from the company Silab under the trademark Firmalift® or from the company LSN under the trademark Cytovitin®; an extract of *Laminaria ochroleuca* such as Laminaine® from Secma; the essence of Mamaku from Lucas Meyer, the extract of lupin marketed by Silab under the trademark Structurine®; the extract of *Fagus sylvatica* beech buds marketed by Gattefosse under the trademark Gatuline® RC.

Agents for Stimulating Fibroblast or Keratinocyte Proliferation and/or Keratinocyte Differentiation:

The agents for stimulating fibroblast proliferation that may be used in the composition according to the invention may be selected, for example, from plant proteins or polypeptides, extracted especially from soybean (for example a soybean extract marketed by LSN under the trademark Eleseryl SH-VEG 8® or marketed by Silab under the trademark Raffermine®); an extract of hydrolysed soybean proteins such as Ridulisse® from Silab; and plant hormones such as gibberellins and cytokinins; a peptide extract of hazelnut such as the product marketed by Solabia under the trademark Nuteline C®.

Preferably, an agent that promotes keratinocyte proliferation and/or differentiation will be used.

The agents for stimulating keratinocyte proliferation that may be used in the composition according to the invention especially comprise adenosine; phloroglucinol, the extract of *Hydrangea macrophylla* leaves, for instance Amacha Liquid E® from Ichimaru Pharcos, a yeast extract such as Stimoderm® from CLR; the extract of *Larrea divaricata* such as Capislow® from Sederma, mixtures of extract of papaya, of olive leaves and of lemon, such as Xyleine® from Vincience, retinol and esters thereof, including retinyl palmitate, phloroglucinol, the nut cake extracts marketed by the Gattefosse and the extracts of *Solanum tuberosum* such as Dermolectine® marketed by Sederma.

Among the agents for stimulating keratinocyte differentiation are, for example, minerals such as calcium; sea fennel, a peptide extract of lupin, such as the product marketed by Silab under the trademark Structurine®; sodium beta-sitosteryl sulfate, such as the product marketed by Seporga under the trademark Phytocohesine®; and a water-soluble extract of corn, such as the product marketed by Solabia under the trademark Phytovityl®; a peptide extract of *Voandzeia substerranea* such as the product marketed by Laboratoires Sérobiologiques under the trademark Filladyn LS 9397®; and lignans such as secoisolariciresinol, and retinol and esters thereof, including retinyl palmitate.

As agents for stimulating keratinocyte proliferation and/or differentiation, mention may also be made of oestrogens such as oestradiol and homologues; cytokines.

As preferred active agents for stimulating fibroblast or keratinocyte proliferation and/or keratinocyte differentiation, mention will be made of plant proteins or polypeptides, extracted especially from soybean (for example a soybean extract marketed by LSN under the trademark Eleseryl SH-VEG 8® or marketed by Silab under the trademark Raffermine®); an extract of hydrolysed soybean proteins such as Ridulisse® from Silab; a peptide extract of hazelnut such as the product marketed by Solabia under the trademark Nuteline C®; adenosine; phloroglucinol, a yeast extract such as Stimoderm® from CLR; a peptide extract of lupin such as the product marketed by Silab under the trademark Structurine®; a water-soluble corn extract, such as the product marketed by Solabia under the trademark Phytovityl®; a peptide extract of *Voandzeia substerranea*, such as the product marketed by Laboratoires Serobiologiques under the trademark Filladyn LS 9397®; retinol and esters thereof, including retinyl palmitate.

Agents for Promoting the Maturation of the Horny Envelope:

Agents that participate in the maturation of the horny envelope, which becomes impaired with age and induces a decrease in transglutaminase activity, may be used in the compositions of the invention. Examples that may be mentioned include urea and derivatives thereof and in particular Hydrovance® from National Starch and the other active agents mentioned in L'Oréal FR-2,877,220 (unpublished).

NO-Synthase Inhibitors:

The agent with an inhibitory action on NO synthase may be selected from among OPCs (procyannidol oligomers); plant extracts of the species *Vitis vinifera* marketed especially by Euromed under the trademark "Leucocyanidines de raisins extra", or by Indena under the trademark Leucoselect®, or finally by Hansen under the trademark "Extrait de marc de raisin"; plant extracts of the species *Olea europaea* preferably obtained from olive tree leaves and marketed especially by Vinyals in the form of a dry extract, or by Biologia & Technologia under the trademark Eurol® BT; and plant extracts of the species *Gingko biloba*, preferably a dry aqueous extract of this plant marketed by Beaufour under the trademark "*Ginkgo biloba* extrait standard", and mixtures thereof.

Peripheral Benzodiazepine Receptor (PBR) Antagonists:

Mention may be made, for example, of 1-(2-chlorophenyl)-N-(1-methylpropyl)-3-isoquinoline carboxamide; the compounds described in patent applications WO 03/030 937 and WO 03/068 753, pyridazino[4,5-b]indole-1-acetamide derivatives of general formula (VII) as described in WO 00/44384.

Agents for Increasing the Activity of the Sebaceous Glands:

Mention may be made, for example, of methyl dehydrojasmonate, hecogenin, hedione and O-linoleyl-6D-glucose, and mixtures thereof.

Agents for Stimulating the Energy Metabolism of Cells:

The active agent for stimulating the energy metabolism of cells may be selected, for example, from biotin, an extract of *Saccharomyces cerevisiae* such as Phosphovital® from Sederma, the mixture of sodium, manganese, zinc and magnesium salts of pyrrolidonecarboxylic acid, for instance Physiogenyl® from Solabia, a mixture of zinc, copper and magnesium gluconate, such as Sepitonic M3® from SEPPIC, and mixtures thereof; a beta-glucan derived from *Saccharomyces cerevisiae*, such as the product marketed by Mibelle AG Biochemistry.

Tensioning Agents:

The term "tensioning agent" that may be used according to the invention means compounds liable to have a tensioning effect, i.e., being able to make the skin taut.

According to the invention, the term "tensioning agent" generally means any polymer that is soluble or dispersible in water at a temperature ranging from 25° C. to 50° C. at a concentration of 7% by weight in water or at the maximum concentration at which a medium of uniform appearance is formed and producing at this concentration of 7% or at this maximum concentration in water a shrinkage of more than 15% in the test described below.

The maximum concentration at which a medium of uniform appearance forms is determined to within ±10% to preferably to within ±5%.

The expression "medium of uniform appearance" means a medium that does not contain any aggregates that are visible to the naked eye.

For the determination of the said maximum concentration, the tensioning agent is gradually added to the water with deflocculating stirring at a temperature ranging from 25° C. to 50° C., and the mixture is then stirred for one hour. The mixture thus prepared is then examined after 24 hours to see if it is of uniform appearance (absence of aggregates visible to the naked eye).

The tensioning effect may be characterized by an in vitro shrinkage test.

A homogeneous mixture of the tensioning agent in water, at a concentration of 7% by weight or at the maximum concentration defined above, is prepared beforehand and as described previously.

30 µl of the homogeneous mixture are placed on a rectangular sample (10×40 mm, thus having an initial width $L_0$ of 10 mm) of elastomer with a modulus of 20 MPa and a thickness of 100 µm.

After drying for 3 hours at 22±3° C. and 40±10% relative humidity RH, the elastomer sample has a shrunken width, noted $L_{3h}$, due to the tension exerted by the applied tensioning agent.

The tensioning effect (TE) of the said polymer is then quantified in the following manner:

'TE'=$(L_0-L_{3h}/L_0)$×100 as % with $L_0$=initial width 10 mm and
$L_{3h}$=width after 3 hours of drying

The tensioning agent may be selected from among: plant or animal proteins and hydrolysates thereof;
  polysaccharides of natural origin;
  mixed silicates;
  colloidal particles of mineral fillers;
  synthetic polymers;
  and mixtures thereof.

One skilled in the art will know how to choose, from the chemical categories listed above, the materials corresponding to the tensioning test as described below.

Mention May be Made Especially of:

(a) plant proteins and protein hydrolysates, in particular of corn, rye, wheat, buckwheat, sesame, spelt, pea, bean, lentil, soybean and lupin, (b) polysaccharides of natural origin, especially (a) polyholosides, for example (i) in the form of starch derived especially from rice, corn, potato, cassava, pea, wheat, oat, etc. or (ii) in the form of carrageenans, alginates, agars, gellans, cellulose polymers and pectins, advantageously as an aqueous dispersion of gel microparticles, and (b) latices consisting of shellac resin, sandarac gum, dammar resins, elemi gums, copal resins, cellulose derivatives, and mixtures thereof, (c) mixed silicates, especially phyllosilicates and in particular Laponites, (d) colloidal particles of mineral fillers with a number-average diameter of from 0.1 and 100 nm and preferably from 3 and 30 nm, and selected, for example, from: silica, silica-alumina composites, cerium oxide, zirconium oxide, alumina, calcium carbonate, barium sulfate, calcium sulfate, zinc oxide and titanium dioxide. As silica-alumina composite colloidal particles that may be used in the compositions according to the invention, examples that may be mentioned include those marketed by Grace under the trademarks Ludox AM, Ludox AM-X 6021, Ludox HSA and Ludox TMA, (e) synthetic polymers, such as polyurethane latices or acrylic-silicone latices, in particular those described in EP-1,038,519, such as a polydimethylsiloxane grafted with propylthio(polymethyl acrylate), propylthio(polymethyl methacrylate) and propylthio(polymethacrylic acid), or alternatively a polydimethylsiloxane grafted with propylthio(polyisobutyl methacrylate) and propylthio(polymethacrylic acid).

Such grafted silicone polymers are especially marketed by 3M under the trademarks VS 80, VS 70 and LO21.

The tensioning agent will be present in the composition in an amount that is effective for obtaining the desired biological effect according to the invention.

By way of example, the tensioning agent may be included in the composition according to the invention in a content ranging from 0.01% to 30% by weight of active material and preferably from 1% to 30% by weight of active material relative to the total weight of the composition.

The term "active material" is intended to exclude the medium in which the tensioning agent may be dissolved or dispersed in its commercial form, for example in the case of dispersions of colloidal particles.

It is also possible, especially in order to complement and/or potentiate the effect of tensioning agents, to use agents that increase the expression of mechanoreceptors, such as agents that increase the expression of integrins.

An example that may be mentioned is an extract of rye seed, such as the product marketed by Silab under the trademark Coheliss®.

Fat-Restructuring Agents;

According to the invention, the term "fat-restructuring agents" means agents capable of stimulating lipogenesis and of promoting adipocyte differentiation, thus making it possible to prevent or slow down the wasting of fat contained in the skin-supporting tissues, also known as "wasting of skin fat".

The term "skin fat" means the network of fat cells that forms the volumes on which the facial skin rests and is molded.

These Agents are Intended:

to reduce the loss of skin density and/or the wasting of skin fat, in particular on the cheeks and around the eyes, and/or to prevent the collapse and/or hollowing of the facial volumes, the loss of consistency of the skin and/or its maintenance, in particular on the cheeks and around the eyes, and/or to improve the underlying volumes of the skin of the face and/or the neck, in particular on the cheeks, the oval of the face and around the eyes, and/or to improve the density, springiness and maintenance of the skin, in particular on the cheeks, the oval of the face and around the eyes, and/or to remodel the facial features, in particular the oval of the face.

Examples of fat-restructuring agents that may especially be mentioned include an extract of black tea, such as the extract of fermented black tea marketed by Sederma under the trademark Kombuchka®, and an extract of *Artemisia abrotanum*, such as the product marketed by Silab under the trademark Pulpactyl®.

Slimming Agents:

Slimming (lipolytic) agents that may especially be mentioned include caffeine, theophylline and its derivatives, theobromine, sericosine, asiatic acid, acefylline, aminophylline, chloroethyltheophylline, diprofylline, diniprophylline, etamiphylline and its derivatives, etofylline and proxyphylline; extracts of tea, of coffee, of guarana, of maté, of cola (*Cola nitida*) and especially the dry extract of guarana fruit (*Paulina sorbilis*) containing 8% to 10% caffeine; extracts of climbing ivy (*Hedera helix*), of arnica (*Arnica montana* L), of rosemary (*Rosmarinus officinalis* N), of marigold (*Calendula officinalis*), of sage (*Salvia officinalis* L), of ginseng (*Panax ginseng*), of St.-John's wort (*Hypericum perforatum*), of butcher's-broom (*Ruscus aculeatus* L), of meadowsweet (*Filipendula ulmaria* L), of orthosiphon (*Orthosiphon stamincus Benth*), of birch (*Betula alba*), of pumpwood and of argan tree, extracts of *ginkgo biloba*, extracts of horsetail (*Equisetum arvense*), extracts of escin (*Aesculus hippocastanum*), extracts of cangzhu, extracts of *Chrysanthellum indicum*, extracts of diosgenin-rich *Dioscorea* plants or pure diosgenin or hecogenin and derivatives thereof, extracts of Ballota, extracts of *Guioa*, of *Davallia*, of *Terminalia*, of *Barringtonia*, of *Trema* or of *Antirobia*, the extract of bitter orange pips (*Citrus bigarradia*); an extract of husks of cocoa beans (*Theobroma cacao*) such as the product marketed by Solabia under the trademark Caobromine®.

Agents for Promoting the Cutaneous Microcirculation:

The active agent acting on the cutaneous microcirculation may be used for preventing dulling of the complexion and/or to improve the appearance of the area around the eyes, in particular to reduce the shadows around the eyes. It may be selected, for example, from an extract of maritime pine bark, for instance Pycnogenol® from Biolandes, manganese gluconate (Givobio GMn® from SEPPIC), an extract of *Ammi visnaga* such as Visnadine from Indena, extract of lupin (Eclaline® from Silab), the protein coupling of hydrolysed wheat/palmitic acid with palmitic acid, such as Epaline 100 from Laboratoires Carilène, the extract of bitter orange blossom (Remoduline® from Silab), vitamin P and derivatives thereof, for instance methyl-4 esculetol sodium monoethanoate marketed under the trademark Permethol® by Sephytal, extracts of *Ruscus*, of common horse chestnut, of ivy, of ginseng and of melilot, caffeine, nicotinate and derivatives thereof, lysine and derivatives thereof, for instance Asparlyne® from Solabia, an extract of black tea such as Kombuchka from Sederma; rutin salts; an extract of the alga *Corallina officinalis*, such as the product marketed by Codif; and mixtures thereof.

As preferred agents for promoting the cutaneous microcirculation, mention will be made of caffeine, an extract of bitter orange blossom, an extract of black tea, rutin salts and an extract of the alga *Corallina officinalis*.

Calmatives or Anti-Irritants:

The term "calmative" means a compound that can reduce the sensation of stinging, itching or tautness of the skin.

As calmatives that may be used in the composition according to the invention, mention may be made of: procyannidol oligomers, vitamins E, B5 and B3, caffeine and derivatives thereof, pentacylic triterpenes and plant extracts containing them, β-glycyrrhetinic acid and salts or derivatives thereof (stearyl glycyrrhetate, 3-stearoyloxyglycyrrhetic acid or glycyrrhetinic acid monoglucuronide) and also plants containing them (e.g.: *Glycyrrhiza glabra*), oleanolic acid and salts thereof, ursolic acid and salts thereof, boswellic acid and salts thereof, betulinic acid and salts thereof, an extract of *Paeonia suffruticosa* and/or *lactiflora*, an extract of *Laminaria saccharina*, extracts of *Centella asiatica*, Canola oil, bisabolol, the phosphoric diester of vitamin E and C, for instance Sepivital EPC® from SEPPIC, camomile extracts, allantoin, omega-3 unsaturated oils such as musk rose oil, blackcurrant oil, Ecchium oil, fish oil or beauty-leaf oil, plankton extracts, capryloyl glycine, a mixture of water lily blossom extract and of palmitoylproline, such as the product marketed under the trademark Seppicalm VG® by SEPPIC, an extract of *Boswellia serrata*, an extract of *Centipeda cunninghami*, such as the product marketed under the trademark Cehami PF® by TRI-K Industries, an extract of sunflower seeds, in particular Hélioxine® from Silab, an extract of *Linum usitatissimum* seeds, for instance Sensiline® from Silab, tocotrienols, piperonal, an extract of *Epilobium angustifolium*, such as the product marketed under the trademark Canadian Willowherb Extract by Fytokem Products, Aloe vera, phytosterols, cornflower water, rose water, an extract of mint, in particular of mint leaves, for instance Calmiskin® from Silab, aniseed derivatives, filamentous bacteria, for instance *Vitreoscilla filiformis* as described in patent EP 761 204 and marketed by Chimex under the trademark Mexoryl SBG®, an extract of rose petals, for instance Rose Flower Herbasol® extract from the company Cosmetochem, shea butter, a mixture of the waxy fraction of barley seeds obtained by supercritical $CO_2$, of shea butter and of argan oil, for instance Stimu-tex AS® from Pentapharm, alkaline-earth metal salts, especially of strontium, a fermented extract of Alteromonas marketed under the trademark Abyssine® by Atrium Biotechnologies; spring water from the Vichy basin, such as waters originating from the Célestin, Chomel, Grande-Grille, Hôpital, Lucas and Parc sources, and preferably water from the Lucas source; an extract of *Eperua falcata* bark, such as the product marketed by Cognis under the trademark Eperuline®; an extract of *Paeonia suffruticosa* root, such as the product marketed by Ichimaru Pharcos under the trademark Botanpi Liquid B®; and mixtures thereof.

As preferred calmatives according to the invention, use will be made of:

β-glycyrrhetinic acid and salts or derivatives thereof (stearyl glycyrrhetate, 3-stearoyloxyglycyrrhetic acid or glycyrrhetinic acid monoglucuronide) and also plants containing them (e.g., *Glycyrrhiza glabra*); ursolic acid and salts thereof; extracts of *Centella asiatica*, Canola oil, bisabolol; camomile extracts, allantoin; a mixture of extract of water lily blossom and of palmitoylproline, such as the product marketed under the trademark Seppicalm VG® by SEPPIC; Aloe vera, rose water, extract of mint, in particular of mint leaves, such as Calmiskin® from Silab, filamentous bacteria such as *Vitreoscilla filiformis* as described in patent EP 761 204 and marketed by Chimex under the trademark Mexoryl SBG®, an extract of rose petals such as Rose Flower Herbasol® extract from the company Cosmetochem, shea butter, a fermented extract of Alteromonas marketed under the trademark Abyssine® by Atrium Biotechnologies; spring water from the Vichy basin, such as waters originating from the Celestin, Chomel, Grande-Grille, Hôpital, Lucas and Parc sources, and preferably water from the Lucas source; an extract of *Eperua falcata* bark, such as the product marketed by Cognis under the trademark Eperuline®; an extract of *Paeonia suffruticosa* root, such as the product marketed by Ichimaru Pharcos under the trademark Botanpi Liquid B®; and mixtures thereof.

Sebo-Regulating or Anti-Seborrhoeic Agents:

The term "sebo-regulating or anti-seborrhoeic agents" especially means agents capable of regulating the activity of the sebaceous glands.

Mention may be made especially of:

retinoic acid, benzoyl peroxide, sulfur, vitamin B6 (or pyridoxine), selenium chloride and sea fennel;

mixtures of extract of cinnamon, of tea and of octanoylglycine such as Sepicontrol A5 TEA from SEPPIC;

the mixture of cinnamon, sarcosine and octanoylglycine marketed especially by SEPPIC under the trademark Sepicontrol A5®;

zinc salts such as zinc gluconate, zinc pyrrolidonecarboxylate (or zinc pidolate), zinc lactate, zinc aspartate, zinc carboxylate, zinc salicylate and zinc cysteate;

copper derivatives and in particular copper pidolate such as Cuivridone® from Solabia;

extracts of plants of the species *Arnica montana, Cinchona succirubra, Eugenia caryophyllata, Humulus lupulus, Hypericum perforatum, Mentha piperita, Rosmarinus oficinalis, Salvia oficinalis* and *Thymus vulgaris*, all marketed, for example, by Maruzen;

extracts of meadowsweet (*Spiraea ulmaria*), such as the product marketed under the trademark Sebonormine® by Silab; extracts of the alga *Laminaria saccharina*, such as the product marketed under the trademark Phlorogine® by Biotechmarine;

mixtures of extracts of salad burnet root (*Sanguisorba officinalis/Poterium officinale*), of ginger rhizomes (*Zingiber officinalis*) and of cinnamon bark (*Cinnamomum cassia*), such as the product marketed under the trademark Sebustop® by Solabia;

linseed extracts, such as the product marketed under the trademark Linumine® by Lucas Meyer;

Phellodendron extracts, such as those marketed under the trademark Phellodendron extract BG by Maruzen or Oubaku liquid B by Ichimaru Pharcos;

mixtures of argan oil, of *Serenoa serrulata* (saw palmetto) extract and of sesame seed extract, such as the product marketed under the trademark Regu SEB® by Pentapharm;

mixtures of extracts of willowherb, of *Terminalia chebula*, of nasturtium and of bioavailable zinc (microalgae), such as the product marketed under the trademark Seborilys® by Green Tech;

extracts of *Pygeum afrianum*, such as the product marketed under the trademark *Pygeum afrianum* sterolic lipid extract by Euromed;

extracts of *Serenoa serrulata*, such as the products marketed under the trademark Viapure Sabal by Actives International or those marketed by Euromed;

mixtures of extracts of plantain (*Plantago* sp.), of *Berberis aquifolium* and of sodium salicylate, such as the product marketed under the trademark Seboclear® by Rahn;

clove extract, such as the product marketed under the trademark Clove extract powder by Maruzen;

argan oil, such as the product marketed under the trademark Lipofructyl® by Laboratoires Sérobiologiques;

lactic protein filtrates, such as the product marketed under the trademark Normaseb® by Sederma;

extracts of the alga *Laminaria*, such as the product marketed under the trademark Laminarghane® by Biotechmarine;

oligosaccharides of the alga *Laminaria digitata*, such as the product marketed under the trademark Phycosaccharide AC by Codif;

sugar cane extracts, such as the product marketed under the trademark Policosonol® by Sabinsa;

sulfonated shale oil, such as the product marketed under the trademark Ichthyol Pale® by Ichthyol;

European meadowsweet (*Spiraea ulmaria*) extracts, such as the product marketed under the trademark Cytobiol® Ulmaire by Libiol;

sebacic acid, especially marketed in the form of a sodium polyacrylate gel under the trademark Sebosoft® by Sederma;

glucomannans extracted from konjac tuber and modified with alkylsulfonate chains, such as the product marketed under the trademark Biopol Beta by Arch Chemical;

extracts of *Sophora angustifolia*, such as those marketed under the trademark *Sophora* powder or *Sophora* extract by Bioland;

extracts of *Cinchona succirubra* bark, such as the product marketed under the trademark Red Bark HS by Alban Muller;

extracts of *Quillaja saponaria*, such as the product marketed under the trademark Panama wood HS by Alban Muller;

glycine grafted onto an undecylenic chain, such as the product marketed under the trademark Lipacide UG OR by SEPPIC;

the mixture of oleanolic acid and of nordihydroguaiaretic acid, such as the product marketed in the form of a gel under the trademark AC.Net by Sederma;

phthalimidoperoxyhexanoic acid;

tri($C_{12}$-$C_{13}$)alkyl citrate marketed under the trademark Cosmacol® ECI by Sasol; tri($C_{14}$-$C_{15}$)alkyl citrate marketed under the trademark Cosmacol® ECL by Sasol;

10-hydroxydecanoic acid, and especially mixtures of 10-hydroxydecanoic acid, of sebacic acid and of 1,10-decanediol, such as the product marketed under the trademark Acnacidol® BG by Vincience; and mixtures thereof.

Preferred anti-seborrhoeic active agents that may be mentioned include:

benzoyl peroxide and vitamin B6 (or pyridoxine), zinc salts such as zinc gluconate, zinc pyrrolidonecarboxylate (or zinc pidolate), zinc lactate, zinc aspartate, zinc carboxylate, zinc salicylate and zinc cysteate;

meadowsweet (*Spiraea ulmaria*) extracts, such as the product marketed under the trademark Sebonormine® by Silab;

extracts of the alga *Laminaria saccharina*, such as the product marketed under the trademark Phlorogine® by Biotechmarine;

mixtures of extracts of salad burnet root (*Sanguisorba officinalis/Poterium officinale*), of ginger rhizomes (*Zingiber officinalis*) and of cinnamon bark (*Cinnamomum cassia*), such as the product marketed under the trademark Sebustop® by Solabia;

clove extract, such as the product marketed under the trademark Clove extract powder by Maruzen;

lactic protein filtrates, such as the product marketed under the trademark Normaseb® by Sederma;

European meadowsweet (*Spiraea ulmaria*) extracts, such as the product marketed under the trademark Cytobiol® Ulmaire by Libiol;

sebacic acid, especially marketed in the form of a sodium polyacrylate gel under the trademark Sebosoft® by Sederma;

glycine grafted onto an undecylenic chain, such as the product marketed under the trademark Lipacide UG OR by SEPPIC;

tri($C_{12}$-$C_{13}$)alkyl citrate marketed under the trademark Cosmacol® ECI by Sasol; tri($C_{14}$-$C_{15}$)alkyl citrate marketed under the trademark Cosmacol® ECL by Sasol;

10-hydroxydecanoic acid, and especially mixtures of 10-hydroxydecanoic acid, of sebacic acid and of 1,10-decanediol, such as the product marketed under the trademark Acnacidol® BG by Vincience; and mixtures thereof.

Preferentially, the anti-seborrhoeic active agent is selected from among:

zinc salts such as zinc gluconate, zinc pyrrolidonecarboxylate (or zinc pidolate), zinc lactate, zinc aspartate, zinc carboxylate, zinc salicylate and zinc cysteate; and preferably zinc pyrrolidonecarboxylate (or zinc pidolate) or zinc salicylate;

clove extract, such as the product marketed under the trademark Clove extract powder by Maruzen;

glycine grafted onto an undecylenic chain, such as the product marketed under the trademark Lipacide UG OR by SEPPIC;

tri($C_{12}$-$C_{13}$)alkyl citrate marketed under the trademark Cosmacol® ECI by Sasol; tri($C_{14}$-$C_{15}$)alkyl citrate marketed under the trademark Cosmacol® ECL by Sasol;

and mixtures thereof.

The anti-seborrhoeic active agent is, for example, present in a content ranging from 0.1% to 10% by weight, preferably from 0.1% to 5% by weight and preferentially from 0.5% to 3% by weight relative to the total weight of the composition.

Astringents:

According to the invention, the term "astringents" means agents for combating the dilation of the sebaceous follicles.

As astringents that may be used in the composition according to the invention, mention may be made of extracts of mushroom pulp (*Polyporus officinalis*), for instance Laricyl LS8865® from Cognis, extracts of *Terminalia catappa* and *Sambucus nigra*, for instance Phytofirm LS9120® from Cognis, extracts of gall nut, for instance Tanlex VE from Ichimaru Pharcos, aluminum hydroxychloride, *centella* extracts (e.g., *Plantactiv centella* from Cognis), dicetyl dimethylammonium chloride, for instance Varisoft 432 CG® from Degussa, common horsechestnut extracts, mallow extracts, witch-hazel extracts, sweet almond extracts, marshmallow root extracts and linseed extracts, for instance Almondermin LS 3380® from Cognis, burdock extracts, nettle extracts, birch extracts, horsetail extracts, camomile extracts, for instance those marketed under the trademark Extrapone 9 Special® by Symrise, skullcap extracts, European meadowsweet extracts (for example Cytobiol Ulmaire from Libiol), a mixture of extracts of white ginger, of horsetail, of nettle, of rosemary and of yucca, for instance Herb extract B1348® from Bell Flavors & Fragrances, extracts of acacia, of elm, of white willow, of cinnamon, of birch and of meadowsweet, Panama sapogenins, zinc phenolsulfonate from Interchemical, extracts of gentian, of cucumber and of walnut, the mixture of extracts of Ratanhia, of grapefruit, of gumweed and of oak gall, for instance Epilami® from Alban Muller.

As preferred astringents according to the invention, use will be made of skullcap extracts, European meadowsweet extracts, meadowsweet extracts, gentian extracts and burdock extracts, and mixtures thereof.

Cicatrizing Agents:

Examples of cicatrizing agents that may especially be mentioned include:

allantoin, urea, certain amino acids, for instance hydroxyproline, arginine, and serine, and also extracts of white lily (for instance Phytélène Lys 37EG 16295 from Indena), a yeast extract, for instance the cicatrizing agent LS LO/7225B from Laboratoires Sérobiologiques), tamanu oil, extract of *Saccharomyces cerevisiae*, for instance Biodynes® TRF® from Arch Chemical, oat extracts, chitosan and derivatives, for instance chitosan glutamate, carrot extracts, artemia extract, for instance GP4G® from Vincience, sodium acexamate, lavandin extracts, propolis extracts, ximeninic acid and salts thereof, rose hip oil, marigold extracts, for instance Souci Armi® Liposoluble from Alban Müller, horsetail extracts, lemon peel extracts, for instance Herbasol® citron from Cosmetochem, *helichrysum* extracts, common yarrow extracts and folic acid.

As preferred cicatrizing agents according to the invention, use will be made of arginine, serine, folic acid, tamanu oil, sodium acexamate, horsetail extracts and *helichrysum* extracts, and mixtures thereof.

Anti-Inflammatory Agents:

As particular anti-inflammatory agents that may be used according to the invention, mention may be made of cortisone, hydrocortisone, indomethacin, betamethasone, azelaic acid, acetaminophen, diclofenac, clobetasol propionate, folic acid; an extract of *Eperua falcata* bark, such as the product marketed by Cognis under the trademark Eperuline®; an extract of *Paeonia suffruticosa* root, such as the product marketed by Ichimaru Pharcos under the trademark Botanpi Liquid B®; and mixtures thereof.

Preferred anti-inflammatory agents that will be mentioned are azelaic acid, folic acid, an extract of *Eperua falcata* bark, such as the product marketed by Cognis under the trademark Eperuline®; an extract of *Paeonia suffruticosa* root, such as the product marketed by Ichimaru Pharcos under the trademark Botanpi Liquid B®; and mixtures thereof.

Anti-Acne Agents:

In one advantageous aspect of the invention, the composition may also comprise at least one anti-acne active agent.

The term "anti-acne active agent" especially means any active agent that has effects on the specific flora of greasy skin, for instance *Propionibacterium acnes* (*P. acnes*). These effects may be bactericidal.

Antibactericidal active agents that may especially be mentioned include:

active agents and preserving agents with antimicrobial activity mentioned in DE-103,24,567, which is incorporated into the present invention by reference, Asiatic acid, the monoethanolamine salt of 1-hydroxy-4-methyl 6-trimethylpentyl-2-pyridone (INCI name: piroctone olamine), marketed especially under the trademark Octopirox® by Clariant;

citronellic acid, perillic acid (or 4-isopropenylcyclohex-1-enecarboxylic acid), glyceryl 2-ethylhexyl ether (INCI name: ethylhexylglycerine), for example marketed under the trademark Sensiva SC 50® by Shulke & Mayr, glyceryl caprylate/caprate, for example marketed under the trademark Capmul MCM® by Abitec;

sodium calcium phosphosilicate, especially marketed under the trademarks Bioactive Glasspowder® and Actysse Premier BG® by Schott Glass;

silver-based particles, for example those marketed under the trademark Metashine ME 2025 PS® by Nippon Sheet Glass;

hop cone extract (*Humulus lupulus*) obtained by supercritical $CO_2$ extraction, such as the product marketed under the trademark HOP CO2-TO Extract® by Flavex Naturextrakte, St.-John's Wort extract obtained by supercritical $CO_2$ extraction, such as the product marketed under the trademark St.-John's Wort $CO_2$-TO Extract® by Flavex Naturextrakte, the mixture of extracts of roots of *Scutellaria baicalensis*, of *Paeonia suffruticosa* and *Glycyrrhiza glabra*, such as the product marketed under the trademark BMB-CF® by Naturogin, argan tree extract, for instance Argapure LS9710 from Cognis;

bearberry leaf extracts, for instance the product marketed under the trademark Melfade-J by Pentapharm;

10-hydroxy-2-decanoic acid such as Acnacidol P® from Vincience, sodium ursolate, azelaic acid, diiodomethyl p-tolyl sulfone such as Amical Flowable® from Angus, malachite powder, zinc oxide such as Zincare® from Elementis GMBH, octadecenedioic acid such as Arlatone dioic DCA® from Uniqema; ellagic acid; 2,4,4'-trichloro-2'-hydroxydiphenyl ether (or triclosan), 1-(3',4'-dichlorophenyl)-3-(4'-chlorophenyl)urea (or triclocarban), 3,4,4'-trichlorocarbanilide, 3',4',5'-trichlorosalicylanilide, phenoxyethanol, phenoxypropanol, phenoxyisopropanol, hexamidine isethionate, metronidazole and salts thereof, miconazole and salts thereof, itraconazole, terconazole, econazole, ketoconazole, saperconazole, fluconazole, clotrimazole, butoconazole, oxiconazole, sulfaconazole, sulconazole, terbinafine, ciclopirox, ciclopiroxolamine, undecylenic acid and salts thereof, benzoyl peroxide, 3-hydroxybenzoic acid, 4-hydroxybenzoic acid, phytic acid, N-acetyl-L-cysteine, lipoic acid, azelaic acid and salts thereof, arachidonic acid, resorcinol, 3,4,4'-trichlorocarbanalide, octoxyglycerine or octoglycerine, octanoylglycine such as Lipacid C8G® from SEPPIC, caprylyl glycol, 10-hydroxy-2-decanoic acid, dichlorophenylimidazoldioxolane and derivatives thereof described in patent application WO 93/18743, iodopropynyl butylcarbamate, 3,7,11-trimethyldodeca-2,5,10-trienol or farnesol, phytosphingosines; quaternary ammonium salts, for instance cetyltrimethylammonium salts and cetylpyridinium salts, and mixtures thereof.

Mention may also be made of certain surfactants with an antimicrobial effect, for instance sodium cocoamphoacetate or disodium diacetate such as Miranol C2M Conc. NP, betaines, for instance the cocoyl betaine Genagen KB from Clariant, sodium lauryl ether sulfate, for instance Emal 270 D from Kao, decyl glucoside, for instance Plantacare 2000 UP, branched $C_{12-13}$ dialkyl malates, for instance Cosmacol EMI, propylene glycol monoesters, for instance propylene glycol monolaurate, monocaprylate or monocaprate, lauryldimethylamine betaine, for instance Empigen BB/LS, and also polyquaternary ammoniums such as Quaternium-24 or Bardac 2050 from Lonza and those described in FR-0,108, 283, and mixtures thereof.

As preferred antimicrobial agents, an agent selected from among octoglycerine or octoxyglycerine, and 10-hydroxy-2-decanoic acid, and mixtures thereof, will be used in the compositions of the invention.

Other additional anti-acne active agents may be added to the abovementioned anti-acne active agents.

Mention may be made especially of active agents with bacterial anti-adhesion effects or agents that act on the biofilm of bacteria to prevent them from multiplying.

As agents for preventing and/or reducing the adhesion of microorganisms, mention may be made especially of: phytanetriol and derivatives thereof as described in EP-1,529, 523, plant oils such as wheatgerm oil, *calendula* oil, castor oil, olive oil, avocado oil, sweet almond oil, groundnut oil, jojoba oil, sesame seed oil, apricot kernel oil, sunflower oil and *macadamia* oil, described in EP-1,133,979, or certain surfactants such as disodium cocoamphodiacetate, oxyethylenated (7 EO) glyceryl cocoate, 18-hexadecenyl succinate, octoxyglyceryl palmitate, octoxyglyceryl behenate, dioctyl adipate, PPG-15 stearyl ether, and the branched $C_{12}$-$C_{13}$ dialkyl tartrates described in EP-1,129,694, and mixtures thereof.

In particular with regard to the propagation of *P. acnes*, or as active agents that act on the biofilm of bacteria to prevent them from proliferating, mention may be made of pentylene glycol, Nylon-66 (polyamide 66 fibers), rice bran oil, polyvinyl alcohol such as Celvol 540 PV Alcohol® from Celanese Chemical, rapeseed oil such as Akorex L® from Karlshamns, and fructose derivatives, and mixtures thereof.

The anti-acne active agent may be present in a content ranging from 0.01% to 10% by weight and preferably from 0.05% to 5% by weight relative to the total weight of the composition.

As a function of the nature and/or solubility of the abovementioned active agents, one skilled in the art will know how to select the most suitable embodiment according to the invention.

The cosmetic and/or dermatological active agents will be present in one of the compositions according to the invention in a content ranging from 0.001% to 20% by weight relative to the total weight of the composition, preferably from 0.01% to 10%, even more preferentially from 0.5% to 5% to more preferably from 0.1% to 1% by weight relative to the total weight of the composition.

For "scrubbing" applications, the contents of cosmetic and/or dermatological active agents may range from 1% to 50% by weight relative to the total weight of the composition and preferably from 1% to 30% by weight relative to the total weight of the composition.

Scrubbing is a well-known means for improving the appearance and/or texture of the skin and/or the scalp, especially for improving the radiance and homogeneity of the complexion and/or for reducing the visible and/or tactile irregularities of the skin, and in particular for improving the surface appearance of the skin, for attenuating actinic lentigo, acne or chickenpox marks, and also for preventing, attenuating or combating the signs of aging of the skin, and especially for smoothing out irregularities in the texture of the skin, such as wrinkles and fine lines.

It has the effect of removing a surface part of the skin to be treated (epidermis and possibly the upper layer of the dermis), via chemical methods.

Other Additional Ingredients:

The composition comprising dehydroascorbic acid or a monomeric, polymeric or isomeric derivative thereof and/or the composition comprising ascorbic acid or a salt or derivative thereof and/or the composition comprising the amine compound may also comprise at least one additional ingredient intended to complement the biological effect of these active agents or to provide an immediate visual effect; mention may be made especially of matting agents, softfocus fillers, fluorescers, and abrasive fillers or exfoliants.

Matting Agents:

The term "matting agent" means agents intended to make the skin visibly more matt and less shiny.

The matting effect of the agent and/or composition containing it may especially be evaluated using a gonioreflectometer, by measuring the ratio R from the specular reflection and the scattered reflection. A value of R of less than or equal to 2 generally reflects a matting effect.

The matting agent may especially be selected from among a rice starch or a corn starch, kaolinite, talc, a pumpkin seed extract, cellulose microbeads, plant fibers, synthetic fibers, in particular polyamide fibers, expanded acrylic copolymer microspheres, polyamide powders, silica powders, polytetrafluoroethylene powders, silicone resin powders, acrylic polymer powders, wax powders, polyethylene powders, powders of elastomeric crosslinked organopolysiloxane coated with silicone resin, talc/titanium dioxide/alumina/silica composite powders, amorphous mixed silicate powders, silicate particles and especially mixed silicate particles, and mixtures thereof.

Examples of matting agents that may especially be mentioned include:

rice or corn starch, in particular an aluminum starch octenyl succinate marketed under the trademark Dry Flo® by National Starch;

kaolinite;

silicas;

talc;

a pumpkin seed extract as marketed under the trademark Curbilene® by Indena;

cellulose microbeads as described in EP-1562562;

fibers, such as silk fiber, cotton fiber, wool fiber, flax fiber, cellulose fiber extracted especially from wood, from vegetables or from algae, polyamide fiber (Nylon®), modified cellulose fiber, poly-p-phenyleneterephthamide fiber, acrylic fiber, polyolefin fiber, glass fiber, silica fiber, aramid fiber, carbon fiber, Teflon® fiber, insoluble collagen fiber, polyester fiber, polyvinyl chloride or polyvinylidene chloride fiber, polyvinyl alcohol fiber, polyacrylonitrile fiber, chitosan fiber, polyurethane fiber, polyethylene phthalate fiber, fibers formed from a mixture of polymers, resorbable synthetic fibers, and mixtures thereof described in EP-1,151, 742;

expanded acrylic copolymer microspheres such as those marketed by EXPANCEL under the trademark Expancel 551®, fillers with an optical effect as described in FR-2,869,796, in particular:

polyamide powders (Nylon®), for instance Nylon 12 particles of the Orgasol type from Arkema, with a mean size of 10 microns and a refractive index of 1.54, silica powders, for instance Silica beads SB150 from Miyoshi with a mean size of 5 microns and a refractive index of 1.45, polytetrafluoroethylene powders, for instance PTFE Ceridust 9205F from Clariant, with a mean size of 8 microns and a refractive index of 1.36, silicone resin powders, for instance the silicone resin Tospearl 145A from GE Silicone with a mean size of 4.5 microns and a refractive index of 1.41, acrylic copolymer powders, especially of polymethyl (meth)acrylate, for instance the PMMA particles Jurymer MBI from Nihon Junyoki, with a mean size of 8 microns and a refractive index of 1.49, or the Micropearl M100® and F 80 ED® particles from the company Matsumoto Yushi-Seiyaku, wax powders, for instance the paraffin wax particles Microease 114S from Micropowders, with a mean size of 7 microns and a refractive index of 1.54, polyethylene powders, especially comprising at least one ethylene/acrylic acid copolymer, and in particular consisting of ethylene/acrylic acid copolymers, for instance the particles Flobeads EA 209 from Sumitomo (with a mean size of 10 microns and a refractive index of 1.48), elastomeric crosslinked organopolysiloxane powders coated with silicone resin, especially with silsesquioxane resin, as described, for example, in U.S. Pat. No. 5,538,793. Such elastomeric powders are marketed under the trademarks KSP-100, KSP-101, KSP-102, KSP-103, KSP-104 and KSP-105 by Shin-Etsu, and talc/titanium dioxide/alumina/silica composite powders such as those marketed under the trademark Coverleaf® AR-80 by Catalyst & Chemicals, mixtures thereof, compounds that absorb and/or adsorb sebum as described in patent application FR 2 869 796. Mention may be made especially of:

silica powders, for instance the porous silica microspheres marketed under the trademark Silica Beads SB-700 marketed by Miyoshi, the products Sunsphere® H51, Sunsphere® H33 and Sunsphere® H53 marketed by Asahi Glass; the polydimethylsiloxane-coated amorphous silica microspheres marketed under the trademark SA Sunsphere® H-33 and SA Sunsphere® H-53 marketed by Asahi Glass;

amorphous mixed silicate powders, especially of aluminum and magnesium, for instance the product marketed under the trademark Neusilin UFL2 by Sumitomo;

polyamide (Nylon®) powders, for instance Orgasol® 4000 marketed by Arkema, and acrylic polymer powders, especially of polymethyl methacrylate, for instance Covabead® LH85 marketed by Wackherr; of polymethyl methacrylate/ethylene glycol dimethacrylate, for instance Dow Corning 5640 Microsponge® Skin Oil Adsorber marketed by Dow Corning, or Ganzpearl® GMP-0820 marketed by Ganz Chemical; of polyallyl methacrylate/ethylene glycol dimethacrylate, for instance Poly-Pore® L200 or Poly-Pore® E200 marketed by Amcol; of ethylene glycol dimethacrylate/lauryl methacrylate copolymer, for instance Polytrap® 6603 marketed by Dow Corning;

silicate particles, such as alumina silicate;

mixed silicate particles, such as:

magnesium aluminum silicate particles, such as saponite or hydrated magnesium aluminum silicate with a sodium sulfate marketed under the trademark Sumecton® by Kunimine;

the magnesium silicate, hydroxyethylcellulose, black cumin oil, marrow oil and phospholipids complex or Matipure® from Lucas Meyer, and mixtures thereof.

Preferred matting agents that may be used according to the invention include a pumpkin seed extract, a rice or corn starch, kaolinite, silicas, talc, polyamide powders, polyethylene powders, acrylic copolymer powders, expanded acrylic copolymer microspheres, silicone resin microbeads and mixed silicate particles, and mixtures thereof.

Fillers with a Soft-Focus Effect:

These fillers may be any material capable of modifying and hiding wrinkles by virtue of their intrinsic physical properties. These fillers may especially modify wrinkles via a tensioning effect, a covering effect or a soft-focus effect.

Examples of fillers that may be given include the following compounds:

porous silica microparticles, for instance the silica beads SB150 and SB700 from Miyoshi with a mean size of 5 μm; the series-H Sunspheres® from Asahi Glass, for instance Sunspheres H33, H51 with respective sizes of 3.5 and 5 μm;

hollow hemispherical silicone resin particles such as NLK 500®, NLK 506® and NLK 510® from Takemoto Oil and Fat, especially described in EP-A-1 579 849;

silicone resin powders, for instance the silicone resin Tospearl® 145A from GE Silicone, with a mean size of 4.5 μm;

acrylic copolymer powders, especially of polymethyl (meth)acrylate, for instance the PMMA particles Jurymer MBI® from Nihon Junyoki, with a mean size of 8 μm, the hollow PMMA spheres marketed under the trademark Covabead® LH85 by Wackherr, and vinylidene/acrylonitrile/methylene methacrylate expanded microspheres marketed under the trademark Expancel®;

wax powders, for instance the paraffin wax particles MicroEase® 114S from MicroPowders, with a mean size of 7 μm;

polyethylene powders, especially comprising at least one ethylene/acrylic acid copolymer, for instance the Flobeads® EA 209 particles from Sumitomo, with a mean size of 10 μm;

crosslinked elastomeric organopolysiloxane powders coated with silicone resin and especially with silsesquioxane resin, under the trademarks KSP-100, KSP-101, KSP-102®, KSP-103®, KSP-104® and KSP-105® by Shin-Etsu;

talc/titanium dioxide/alumina/silica composite powders, for instance those marketed under the trademark Coverleaf AR-80® by Catalyst & Chemicals;

talc, mica, kaolin, lauryl glycine, starch powders crosslinked with octenyl succinate anhydride, boron nitride, polytetrafluoroethylene powders, precipitated calcium carbonate, magnesium carbonate, magnesium hydrogen carbonate, barium sulfate, hydroxyapatite, calcium silicate, cerium dioxide and glass or ceramic microcapsules;

hydrophilic or hydrophobic, synthetic or natural, mineral or organic fibers such as silk fibers, cotton fibers, wool fibers, flax fibers, cellulose fibers extracted especially from wood, vegetables or algae, Polyamide (Nylon®) fibers, modified cellulose fibers, poly-p-terephthamide fibers, acrylic fibers, polyolefin fibers, glass fibers, silica fibers, aramid fibers, carbon fibers, polytetrafluoroethylene (Teflon®) fibers, insoluble collagen fibers, polyester fibers, polyvinyl chloride fibers, polyvinylidene chloride fibers, polyvinyl alcohol fibers, polyacrylonitrile fibers, chitosan fibers, polyurethane fibers, polyethylene phthalate fibers, fibers formed from a mixture of polymers, resorbable synthetic fibers, and mixtures thereof described in EP-1,151,742;

spherical elastomeric crosslinked silicones, for instance Trefil E-505C® or E-506C® from Dow Corning;

abrasive fillers, which, via a mechanical effect, smooth out the skin microrelief, such as abrasive silica, for instance Abrasif SP® from Semanez or nutshell powders (for example of apricot or walnut, from Cosmetochem).

The fillers with an effect on the signs of aging are especially selected from among porous silica microparticles, hollow hemispherical silicones, silicone resin powders, acrylic copolymer powders, polyethylene powders, crosslinked elastomeric organopolysiloxane powders coated with silicone resin, talc/titanium dioxide/alumina/silica composite powders, precipitated calcium carbonate, magnesium carbonate, magnesium hydrogen carbonate, barium sulfate, hydroxyapatite, calcium silicate, cerium dioxide, glass or ceramic microcapsules, and silk fibers or cotton fibers, and mixtures thereof.

The filler may be a soft-focus filler.

The term "soft-focus" filler means a filler which in addition gives the complexion transparency and a hazy effect. Preferably, the soft-focus fillers have a mean particle size of less than or equal to 15 microns. These particles may be in any form and in particular may be spherical or non-spherical. These fillers are more preferably non-spherical.

The soft-focus fillers may be selected from among silica and silicate powders, especially alumina powder, powders of polymethyl methacrylate (PMMA) type, talc, silica/TiO$_2$ or silica/zinc oxide composites, polyethylene powders, starch powders, polyamide powders, styrene/acrylic copolymer powders and silicone elastomers, and mixtures thereof.

Mention may be made in particular of talc with a number-average size of less than or equal to 3 microns, for example talc with a number-average size of 1.8 microns and especially the product marketed under the trademark Talc P3® by Nippon Talc, Nylon® 12 powder, especially the product marketed under the trademark Orgasol 2002 Extra D Nat Cos® by Atochem, silica particles 1% to 2% surface-treated with a mineral wax (INCI name: hydrated silica (and) paraffin) such as the products marketed by Degussa, amorphous silica microspheres, such as the products marketed under the trademark Sunsphere, for example of reference H-53® by Asahi Glass, and silica microbeads such as those marketed under the trademark SB-700 or SB-150® by Miyoshi, this list not being limiting.

The concentration of these fillers with an effect on the signs of aging in the compositions according to the invention may be from 0.1% to 40%, or even from 0.1% to 20% by weight, relative to the total weight of the composition.

Fluorescers:

The term "fluorescer" means a substance which, under the effect of ultraviolet rays and/or visible light, re-emits in the visible region the portion of light that it has absorbed under the same color as that which it naturally reflects. The naturally reflected color is thus reinforced by the re-emitted color and appears extremely bright.

Examples that may be mentioned include colored polyamide and/or formaldehyde/benzoguanamine and/or melamine/formaldehyde/sulfonamide resins, from colored aminotriazine/formaldehyde/sulfonamide co-condensates and/or from metallized polyester flakes and/or mixtures thereof. These fluorescent pigments may also be present in the form of aqueous dispersions of fluorescent pigments.

Mention may also be made of the pink-colored fluorescent aminotriazine/formaldehyde/sulfonamide co-condensate with a mean particle size of 3-4 microns marketed under the trademark Fiesta Astral Pink FEX-1 and the blue-colored fluorescent aminotriazine/formaldehyde/sulfonamide co-condensate with a mean particle size of 3-4.5 microns marketed under the trademark Fiesta Comet Blue FTX-60 by Swada, or alternatively the yellow-colored benzoguanamine/formaldehyde resin covered with formaldehyde/urea resin marketed under the trademark FB-205 Yellow and the red-colored benzoguanamine/formaldehyde resin covered with formaldehyde/urea resin marketed under the trademark FB-400 Orange Red by UK Seung Chemical, and the orange-colored polyamide resin marketed under the trademark Flare 911 Orange 4 by Sterling Industrial Colors.

The fluorescent substances are preferably present in the composition in a content ranging from 0.1% to 20%, preferably from 0.1% to 15% to more preferably from 0.5% to 3% by weight relative to the total weight of the composition.

When the organic fluorescent substances are white, they are also known as optical brighteners.

The optical brightener has the effect of intensifying the radiance and reviving the shades of cosmetic compositions comprising them on application to the skin.

Among the optical brighteners that may be mentioned more particularly are stilbene derivatives, in particular polystyrylstilbenes and triazinestilbenes, coumarin derivatives, in particular hydroxycoumarins and aminocoumarins, oxazole, benzoxazole, imidazole, triazole and pyrazoline derivatives, pyrene derivatives and porphyrin derivatives, and/or mixtures thereof.

Such compounds are available, for example, under the trademarks Tinopal SOP® and Uvitex OB® from the company Ciba Geigy.

The optical brighteners preferentially used are sodium 4,4'-bis[(4,6-dianilino-1,3,5-triazin-2-yl)amino]stilbene-2,2'-disulfonate, 2,5-thiophenediylbis(5-tert-butyl-1,3-benzoxazole) and disodium 4,4'-distyrylbiphenylsulfonate, and/or mixtures thereof.

Abrasive Fillers or Exfoliants:

As exfoliants that may be used in rinse-out compositions according to the invention, examples that may be mentioned include exfoliants for scrubbing particles of mineral, plant or organic origin. Thus, polyethylene beads or powder, Nylon powder, polyvinyl chloride powder, pumice powder, ground apricot kernel or walnut husk, sawdust, glass beads and alumina, and mixtures thereof, may be used, for example.

Mention may also be made of Exfogreen® from Solabia (bamboo extract), extracts of strawberry akenes (Strawberry Akenes from Greentech), peach kernel powder, apricot kernel powder, and finally, in the field of plant powders with an abrasive effect, mention may be made of cranberry kernel powder (*Vaccinium macrocarpus*).

As abrasive fillers or exfoliants that are preferred according to the invention, mention will be made of peach kernel powder, apricot kernel powder, cranberry kernel powder, strawberry akene extracts and bamboo extracts.

The additional ingredient(s) used in one of the care and/or makeup compositions according to the invention may represent from 0.0001% to 20%, preferably from 0.01% to 10% to better still from 0.01% to 1% by weight relative to the total weight of the composition.

In order to further illustrate the present invention and the advantages thereof, the following specific examples are given, it being understood that same are intended only as illustrative and in nowise limitative. In said examples to follow, all parts and percentages are given by weight, unless otherwise indicated.

EXAMPLES

Protocol

The various coloring processes below are performed on samples of Episkin® reconstructed skin inserted into nacelles; which are placed throughout the tests on a Whatmann absorbent paper to obtain an optimal degree of humidity of about 70%. After 4 hours, washing is performed with 1 ml of water. The residual liquid is absorbed with a soft handkerchief. The measurements are taken with a Minolta colorimeter.

For each of these processes, washing is performed with 1 ml of water after 4 hours. The residual liquid is absorbed with a soft handkerchief.

The measurements are taken with a Minolta colorimeter. Colorimetric measurements are then taken.
Equipment
Minolta CM2600d spectrocolorimeter
Illuminant: D65
Observation angle: 10°
SCE: specular excluded The results are expressed in the (L*, a*, b*) system in which L* is the luminance, a* is the red-green axis (−a*=green, +a*=red) and b* is the yellow-blue axis (−b*=blue, +b*=yellow). Thus, a* and b* express the shade of the skin.

The change in coloration relative to untreated control samples is evaluated.

The ratio R=a*/b* makes it possible to estimate the respective contributions of the red and yellow components developed by the skin. The greater the ratio R, the more substantial the red component.

The results are indicated in the following table:
Process A: Dihydroxyacetone (Prior Art):

20 µl of a first solution containing 5% dehydroascorbic acid in a water/ethanol mixture (50/50) are applied to the substrate. After 4 hours, washing is performed with 1 ml of water. The residual liquid is absorbed with a soft handkerchief.

Coloration Processes 1 to 20 According to the Invention:

20 µl of a first solution containing 5% amine compound in a water/ethanol mixture (50/50) and 20 µl of a first solution containing 5% dehydroascorbic acid are applied to the substrate. After 4 hours, washing is performed with 1 ml of water. The residual liquid is absorbed with a soft handkerchief.

| Process | Amine compound used | L* | a* | b* | ΔE* | R (a*/b*) |
|---|---|---|---|---|---|---|
| 1 | L-Phenylalanine | 68.4 | 12.3 | 23.1 | 10.1 | 0.53 |
| 2 | Isoleucine | 73.3 | 5.6 | 20.1 | 8.8 | 0.28 |
| 3 | Methionine | 70.6 | 8.8 | 21.8 | 4.5 | 0.40 |
| 4 | Arginine | 73.5 | 6.2 | 20.2 | 4.3 | 0.31 |
| 5 | Serine | 68.4 | 10.4 | 27.9 | 8.7 | 0.37 |
| 6 | Proline | 71.7 | 5.7 | 27.1 | 5.8 | 0.21 |
| 7 | Alanine | 67.0 | 11.6 | 23.8 | 8.1 | 0.49 |
| 8 | Valine | 55.0 | 5.7 | 14.0 | 16.6 | 0.41 |
| 9 | Glutamine | 71.5 | 10.2 | 21.8 | 18.8 | 0.47 |
| 10 | Tryptophan | 71.2 | 6.5 | 20.9 | 3.9 | 0.31 |
| 11 | Hydroxyproline | 68.3 | 1.9 | 23.6 | 6.0 | 0.08 |
| 12 | Glycine | 72.4 | 8.5 | 26.5 | 8.3 | 0.32 |
| 13 | Glutamic acid | 71.3 | 7.5 | 24.6 | 2.5 | 0.31 |
| 14 | Aspartic acid | 70.8 | 5.0 | 22.2 | 3.5 | 0.22 |
| 15 | Leucine | 77.4 | 4.9 | 21.5 | 6.6 | 0.23 |
| 16 | Tyrosine | 72.5 | 6.9 | 24.2 | 5.9 | 0.28 |
| 17 | Lysine | 73.4 | 4.3 | 20.5 | 4.6 | 0.21 |
| 18 | Taurine | 76.0 | 6.1 | 22.6 | 3.8 | 0.27 |
| 19 | Glutathione | 68.3 | 14.2 | 22.6 | 11.2 | 0.63 |
| 20 | Val-Tyr-Val | 70.7 | 8.5 | 23.3 | 6.3 | 0.36 |
| | Process A with DHA (outside the invention) | 65.6 | 7.4 | 14.1 | 2.8 | 0.52 |

It is observed that, depending on the choice of the amine compound, the processes of the invention make it possible to obtain, relative to DHA alone, colors that darken more quickly and over a more or less light or dark range of shades, the red/yellow component ratio of which may range from 0.08 to 0.53.

Each patent, patent application, publication, text and literature article/report cited or indicated herein is hereby expressly incorporated by reference in its entirety.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A regime or regimen for artificially coloring the skin, comprising topically applying onto the skin of an individual in need of such treatment, a thus effective amount of at least a) dehydroascorbic acid and/or a monomeric derivative thereof of formula (I) below and/or an isomer thereof of formula (I') below and/or a polymeric derivative thereof:

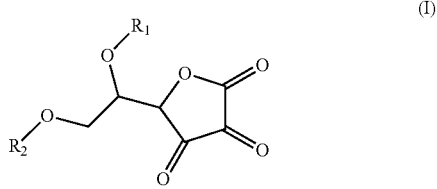

-continued

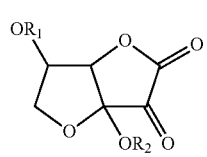

(I')

in which:
OR$_1$ and OR$_2$, which may be identical or different, are each OH; a linear or branched, saturated or unsaturated C$_1$-C$_{30}$ alkoxy radical; a glycoside; a linear or branched, saturated or unsaturated C$_1$-C$_{30}$ aliphatic carboxylic acid ester, optionally substituted with an aryl radical or a heterocycle; an aryl or heterocyclic carboxylic acid ester optionally substituted with at least one linear or branched, saturated or unsaturated C$_1$-C$_{30}$ alkyl radical; a phosphate group; a sulfate group, b) at least one compound comprising at least one free amine function, formulated onto a topically applicable, physiologically acceptable medium therefor, and c) an enzymatic oxidizing agent,
wherein the regime or regimen for artificially coloring the skin is a regime or regimen for artificially darkening the skin, and
wherein the at least one compound having a free amine function is selected from the group consisting of glutathione (GSH), α-amino acids obtained by hydrolysis of animal or plant proteins comprising collagen, keratin, casein, elastin, soya protein, and wheat or almond glutens, arginine, glycine, tyrosine, alanine, phenylalanine, dihydroxyphenylalanine (DOPA), ornithine, lysine, polylysines, spermitine, citrulline, tryptophan, 6-aminocapronic acid, isoleucine, leucine, methionine, serine, proline, valine, hydroxyproline, aspartic acid, tyrosine, taurine, Val-Tyr-Val, L-asparagine, Lys-Lys-Lys-Lys and Cys-Gly.

2. The regime or regimen as defined by claim 1, comprising topically applying a compound of formula (I), dehydroascorbic acid having the structure:

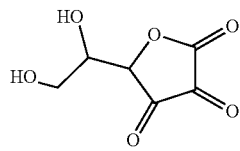

or the isomeric form thereof of formula (I'): 3a,6-dihydroxytetrahydrofuro[3,2-b]furan-2,3-dione having the structure:

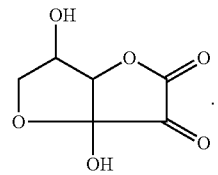 [SMILES: O=C1OC2C(O)COC2(O)C1=O]

3. The regime or regimen as defined by claim 1, in which the dehydroascorbic acid or a monomeric, polymeric or isomeric derivative thereof and the amine compound are stored separately and mixed together at the time of topical application thereof.

4. The regime or regimen as defined by claim 1, comprising also topically applying onto the skin one or more additives selected from among stabilizers, photoprotecting agents, wetting agents, penetrants, colorants, matting fillers, soft-focus fillers, fluorescers, abrasive or exfoliant fillers, and mixtures thereof.

5. The regime or regimen as defined by claim 1, wherein the at least one compound having a free amine function is selected from the group consisting of α-amino acids obtained by hydrolysis of animal or plant proteins comprising collagen, keratin, casein, elastin, soya protein, and wheat or almond glutens, arginine, glycine, tyrosine, alanine, phenylalanine, dihydroxyphenylalanine (DOPA), ornithine, lysine, polylysines, spermitine, citrulline, tryptophan, 6-aminocapronic acid, isoleucine, leucine, methionine, serine, proline, valine, hydroxyproline, aspartic acid, tyrosine, taurine, Val-Tyr-Val, L-asparagine, Lys-Lys-Lys-Lys and Cys-Gly.

6. The regime or regimen as defined by claim 1, wherein the at least one compound having a free amine function is selected from the group consisting of glutathione (GSH), and collagen, keratin, casein, elastin, soya protein, wheat gluten or almond protein hydrolysates.

7. The regime or regimen as defined by claim 1, wherein the enzymatic oxidizing agent comprises a ricases or ascorbate oxidase.

8. The regime or regimen as defined by claim 1, further comprising topically applying onto the skin of an individual in need of such treatment, a thus effective amount of ascorbic acid or a derivative or salt thereof in a topically applicable, physiologically acceptable medium therefor.

* * * * *